United States Patent
Schoenafinger et al.

(10) Patent No.: US 7,781,613 B2
(45) Date of Patent: Aug. 24, 2010

(54) SUBSTITUTED N-AMINOMETHYLENE SULFONAMIDES, PRODUCTION AND USE THEREOF AS MEDICAMENTS

(75) Inventors: Karl Schoenafinger, Alzenau (DE); Stefan Petry, Kelkheim (DE); Guenter Mueller, Sulzbach (DE); Karl-Heinz Baringhaus, Wolfersheim (DE)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/767,660

(22) Filed: Jun. 25, 2007

(65) Prior Publication Data

US 2008/0069851 A1 Mar. 20, 2008

Related U.S. Application Data

(63) Continuation of application No. PCT/EP2006/000313, filed on Jan. 16, 2006.

(30) Foreign Application Priority Data

Jan. 17, 2005 (DE) .................... 10 2005 002 130

(51) Int. Cl.
- *C07C 311/16* (2006.01)
- *A61K 31/18* (2006.01)
- *A61K 31/445* (2006.01)
- *A61K 31/495* (2006.01)
- *C07D 211/26* (2006.01)
- *C07D 265/30* (2006.01)
- *C07D 241/30* (2006.01)

(52) U.S. Cl. ............... 564/84; 514/238.2; 514/252.12; 514/331; 514/602; 544/161; 544/398; 546/229

(58) Field of Classification Search ............ 514/238.2, 514/252.12, 331, 602; 544/161, 398; 546/229; 564/84

See application file for complete search history.

(56) References Cited

U.S. PATENT DOCUMENTS

| | | | |
|---|---|---|---|
| 3,009,910 A | 11/1961 | Ziegler, et. al. | |
| 4,010,273 A | * 3/1977 | Bormann et al. | 514/429 |
| 4,916,149 A | * 4/1990 | Palosi et al. | 514/387 |

FOREIGN PATENT DOCUMENTS

| | | | |
|---|---|---|---|
| DE | 24 61 601 | * | 7/1976 |
| DE | 2518999 | | 11/1976 |
| EP | 0008433 | | 3/1980 |
| EP | 0324184 | | 7/1989 |
| EP | 0324988 | | 7/1989 |
| WO | WO 03/051841 | | 6/2003 |
| WO | WO 03/051842 | | 6/2003 |
| WO | WO 03/105860 | | 12/2003 |
| WO | WO 2004/035550 | | 4/2004 |

OTHER PUBLICATIONS

Novello et al, J. of Organic Chemistry, 1960, vol. 25, 970-981.*
Shani, J., et al., Structure Activity Correlation for Diuretic Furosemide Congeners, Pharmacology, vol. 26, pp. 172-180 (1983).
Neidlein, R., et al., Synthesen, Spektroskopische Eigenschaften Von Alkylmercaptoalkylaminomethylensulfonamiden und Chemisches Reaktionsverhalten Von 1, 1-Bis-(Dimethlamino)-Ethylen, Monatschefte Fur Chemie, vol. 116, pp. 651-660, (1985).

* cited by examiner

*Primary Examiner*—Shailendra Kumar
(74) *Attorney, Agent, or Firm*—Jiang Lin

(57) ABSTRACT

Disclosed are compounds of the general formula (I), with the definitions of the substituents $R^1$ to $R^5$, A and X being detailed in the text, and to their physiologically tolerated salts, to processes for preparing these compounds and to the use thereof as inhibitors of hormone-sensitive lipase (HSL).

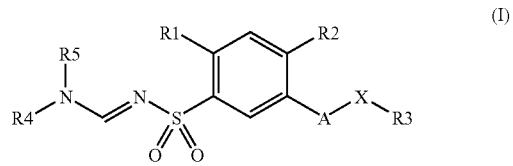

16 Claims, No Drawings

SUBSTITUTED N-AMINOMETHYLENE SULFONAMIDES, PRODUCTION AND USE THEREOF AS MEDICAMENTS

This application is a CON of PCT/EP2006/000313, filed Jan. 16, 2006.

FIELD OF THE INVENTION

The invention relates to compounds of the general formula (I), with the definitions of the substituents $R^1$ to $R^5$, A and X being detailed in the following text, and to their physiologically tolerated salts, to processes for preparing these compounds and to the use thereof as medicament.

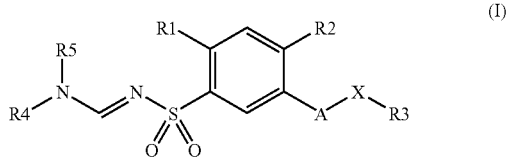

These compounds are inhibitors of hormone-sensitive lipase (HSL).

BACKGROUND OF THE INVENTION

It has been disclosed in the literature that compounds which are suitable as inhibitors of HSL can be employed for the treatment of diabetes mellitus. Thus, benzotriazole derivatives are employed for this purpose in WO 2004/035550. In WO 03/105860 derivatives of boric acid and boric esters, and in WO 03/051842 inter alia amides having a hydrolyzable group, are used as HSL inhibitors. However, the suitability of aminomethylenesulfonamides as HSL inhibitors has not previously been described.

sulfonamide compounds have been disclosed in the literature, which, however, differ from those of the present invention through a different substitution pattern and having different uses (indications).

R. Neidlein et al., Monatshefte für Chemie 116 (1985), pages 651 to 660 describe syntheses and spectroscopic properties of alkylmercaptoalkylaminomethylenesulfonamides. These compounds obligatorily have two aminomethylenesulfonamide substituents in meta position on the benzene fragment, whereas the compounds of the invention have only one such substituent. No connection is made between the compounds described in R. Neidlein et al. and any use as medicaments.

U.S. Pat. No. 3,009,910 describes 2,4-disulfamylanilline derivatives and their use as medicaments with diuretic action. Whereas the methylenesulfonamide substituent is in the position ortho to $R^1$ (for example halogen) and in the position para to $R^2$ (for example —$NH_2$) in the compounds of the invention, this substitution pattern is exactly reversed in the compounds disclosed in U.S. Pat. No. 3,009,910. The methylenesulfonamide substituent is located on the central benzene fragment in the position ortho to an amino substituent and in the position para to a halogen substituent. However, no connection between the compounds described in U.S. Pat. No. 3,009,910 with the treatment of diabetes, or the use of these compounds as inhibitor of HSL, is disclosed in this document.

EP-A 0 008 433 relates to sulfamoylbenzene derivatives and to their use as diuretics and saluretics. The compounds described therein differ from the sulfonamides of the invention to the extent that the central benzene fragment has an unsubstituted sulfamoyl substituent in the position ortho to a halogen substituent. Several routes are indicated for the synthesis of the compounds described in EP-A 0 008 433, the starting materials employed being inter alia the following of the formulae A and B:

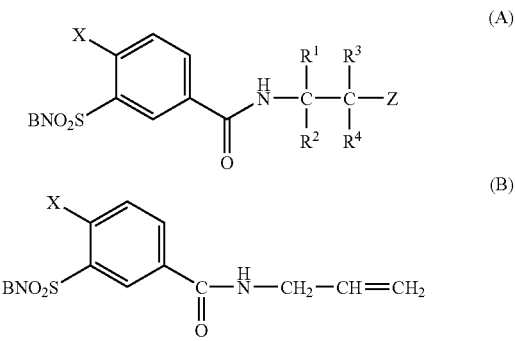

The radicals $R^1$ to $R^4$ in the compounds of the formula A are defined independently of one another as hydrogen or an alkyl radical having 1 to 4 carbon atoms, it being possible for one of the radicals $R^1$ to $R^4$ also to be a carboxyl, hydroxymethyl or an alkyloxycarbonyl group having a maximum of 5 carbon atoms or for one or two of the radicals $R^1$ to $R^4$ to be isopropyl, isobutyl, tert-butyl, phenyl or cycloalkyl having 5 to 6 carbon atoms, X is defined as halogen, Z is defined as leaving group (halogen, hydroxy, trialkylammonium, mesylate or tosylate) and B is defined either as 2 hydrogen atoms or a protective group of the formula =$CR^5$—$NR^6R^7$, where the radicals $R^5$ to $R^7$ may independently of one another be an alkyl group having 1 to 4 carbon atoms and $R^5$ may optionally also be hydrogen. The compounds of the formulae A and B can in each case also be rearranged to intermediate compounds in which the substituent located in the position para to the halogen substituent is defined as —C(O)—O—$CR^3R^4$—$CR^1R^2$—$NH_2$. The aforementioned intermediate compounds which are disclosed as such in EP-A 0 008 433 and for which no use as medicament is described are not an aspect of the present invention.

DE-A 25 18 999 relates to further sulfamylbenzoic acid derivatives which can likewise be used as diuretics or saluretics. Corresponding to EP-A 0 008 433, the pharmaceutically active compounds of the general formula I described in DE-A 25 18 999 also differ through the substitution pattern on the central benzene fragment, which has an amino substituent in the position ortho to a halogen substituent, while the compounds of the invention are unsubstituted at this position. The compounds described in DE-A 25 18 999 are prepared starting from sulfamylbenzoic acid derivatives of a general formula III which have a (—COOR) substituent, where R is hydrogen, an alkyl or cycloalkyl radical having up to 6 carbon atoms, on the central benzene fragment in the position para to the halogen substituent Y. These aforementioned intermediate compounds of the general formula III of DE-A 25 18 999, which are disclosed as such therein and for which no use as medicaments is described, are not an aspect of the present invention.

EP-A 0 324 988 and EP-A 0 324 184 describe further medicinal products with diuretic and saluretic effect, of (in each case) a general formula I, which have an unsubstituted sulfamyl substituent in the position ortho to the chlorine substituent of the central benzene fragment. In addition, the compounds of the formula I in EP-A 0 324 988 have an amide substituent, which is substituted in turn by unsubstituted or at least monosubstituted benzimidazolyl, in the position para to the chlorine substituent; the amide substituent in EP-A 0 324 184 is substituted by unsubstituted or at least monosubstituted (1,2,3,4-tetrahydroisoquinolinyl). In analogy to EP-A 0 008 433, the active pharmaceutical ingredients mentioned in the two aforementioned EP applications are synthesized from precursors which have a dialkylaminomethylenesulfamyl substituent instead of an unsubstituted sulfamyl substituent. The intermediate compounds described in EP-A 0 324 988 and EP-A 0 324 184, which are disclosed as such and for which no use as medicament is described, are not an aspect of the present invention.

SUMMARY OF THE INVENTION

Since diseases such as diabetes mellitus which can be treated by inhibition of HSL represent a serious hazard for the health of humans and other mammals, there is a great need for novel medicaments which have an advantageous therapeutic profile for the treatment of such diseases. The present application is therefore based on the object of providing novel compounds which have an inhibitory effect on HSL.

The object is achieved by substituted N-aminomethylenesulfonamides of the formula (I).

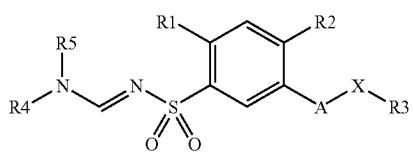

in which the meanings are:

R1 is hydrogen, halogen or —$CF_3$;

R2 is hydrogen, —$NH_2$, —$NH(C_1$-$C_3$-alkyl), —$N(C_1$-$C_3$-alkyl)$_2$ or $C_1$-$C_3$-alkoxy and R1 and R2 may not simultaneously be hydrogen;

R3 is unsubstituted or at least monosubstituted $C_1$-$C_{10}$-alkyl, $C_2$-$C_{10}$-alkenyl, aryl, heterocyclyl or heteroaryl,
where the substituents are selected from the group consisting of:
aryl, heteroaryl, heterocyclyl, aryl-($C_1$-$C_6$-alkyl)-, heterocyclyl-($C_1$-$C_6$-alkyl)-, heteroaryl-($C_1$-$C_6$-alkyl)-, —O-aryl, fluorine, chlorine, bromine, —$CF_3$, —$OCF_3$, —$NO_2$, —CN, —C(O)R7, hydroxy, $C_1$-$C_6$-alkyl and $C_1$-$C_3$-alkoxy,
and the aryl, heteroaryl and heterocyclyl fragments of these substituents may in turn be at least monosubstituted by fluorine, chlorine, bromine, oxo, —$CF_3$, —$OCF_3$, —$NO_2$, —CN, hydroxy, $C_1$-$C_3$-alkyl or $C_1$-$C_3$-alkoxy;

R4 and R5 are independently of one another hydrogen, unsubstituted or at least monosubstituted $C_1$-$C_{10}$-alkyl or aryl-($C_1$-$C_6$-alkyl)-,
where the substituents are selected from the group consisting of: aryl, heteroaryl, heterocyclyl, aryl-($C_1$-$C_6$-alkyl)-, heterocyclyl-($C_1$-$C_6$-alkyl)-, heteroaryl-($C_1$-$C_6$-alkyl)-, —O-aryl, fluorine, chlorine, bromine, —$CF_3$, —$OCF_3$, —$NO_2$, —CN, —C(O)R7, hydroxy, $C_1$-$C_6$-alkyl and $C_1$-$C_3$-alkoxy,
and the aryl, heteroaryl and heterocyclyl fragments of these substituents may in turn be at least monosubstituted by fluorine, chlorine, bromine, oxo, —$CF_3$, —$OCF_3$, —$NO_2$, —CN, hydroxy, $C_1$-$C_3$-alkyl or $C_1$-$C_3$-alkoxy; or R4 and R5 form together with the nitrogen atom to which they are bonded unsubstituted or at least monosubstituted heterocyclyl,
where the substituents are selected from:
halogen, $C_1$-$C_6$-alkyl, $C_1$-$C_6$-alkoxy, phenyl, oxo, —$NH_2$, —$NH(C_1$-$C_3$-alkyl), —$N(C_1$-$C_3$-alkyl)$_2$, —$OCF_3$, —$CF_3$ or hydroxy;

R6 is hydrogen, —$SO_2(C_1$-$C_3$-alkyl), unsubstituted or at least monosubstituted $C_1$-$C_{10}$-alkyl, $C_2$-$C_{10}$-alkenyl or aryl-($C_1$-$C_6$-alkyl)-,
where the substituents are selected from:
halogen, $C_1$-$C_6$-alkyl, $C_1$-$C_6$-alkoxy, phenyl, oxo, —$NH_2$, —$NH(C_1$-$C_3$-alkyl), —$N(C_1$-$C_3$-alkyl)$_2$, —$OCF_3$, —$CF_3$ or hydroxy; or R6 forms, together with R3 and X, if X is N, unsubstituted or at least monosubstituted heterocyclyl,
where the substituents are selected from the group consisting of:
aryl, heteroaryl, heterocyclyl, aryl-($C_1$-$C_6$-alkyl)-, heterocyclyl-($C_1$-$C_6$-alkyl)-, heteroaryl-($C_1$-$C_6$-alkyl)-, —O-aryl, fluorine, chlorine, bromine, —$CF_3$, —$OCF_3$, —$NO_2$, —CN, —C(O)R7, hydroxy, $C_1$-$C_6$-alkyl and $C_1$-$C_3$-alkoxy,
and the aryl, heteroaryl and heterocyclyl fragments of these substituents may in turn be at least monosubstituted by fluorine, chlorine, bromine, oxo, —$CF_3$, —$OCF_3$, —$NO_2$, —CN, hydroxy, $C_1$-$C_3$-alkyl or $C_1$-$C_3$-alkoxy;

R7 is $C_1$-$C_3$-alkoxy, —O-phenyl, $C_1$-$C_3$-alkyl, —$NH_2$, —$NH(C_1$-$C_3$-alkyl), —$N(C_1$-$C_3$-alkyl)$_2$ or phenyl,
and the phenyl fragments of R7 may in turn be at least monosubstituted by fluorine, chlorine, bromine, —$CF_3$, —$OCF_3$, —$NO_2$, —CN, hydroxy, $C_1$-$C_3$-alkyl or $C_1$-$C_3$-alkoxy;

A is $SO_2$, CO or $CH_2$;

X is NR6 or O;

heteroaryl is a 5 to 10-membered, aromatic, mono- or bicyclic heterocycle which comprises one or more heteroatoms selected from N, O and S;

aryl is a 5 to 10-membered aromatic mono- or bicyclic system;

heterocyclyl is a 5 to 10-membered, nonaromatic, mono- or bicyclic heterocycle which comprises one or more heteroatoms selected from N, O and S;

or a physiologically tolerated salt thereof;

with the proviso that when $R^2$ is hydrogen and R1 is halogen, then -A-X-R3 is not i) —C(O)—O—$CH_2$—$CH_2$—$NH_2$, ii) —C(O)—NH—$CH_2$—CH=$CH_2$, iii) —C(O)—NH—$CH_2$—$CH_2$-Z with Z equal to halogen, hydroxy, trialkylammonium, mesylate or tosylate, iv) —C(O)—O—($C_1$-$C_6$-alkyl), v) —C(O)—NH-benzimidazolyl or yl) —C(O)—NH-(1,2,3,4-tetrahydroisoquinolinyl), where the —$CH_2$—$CH_2$— fragment in i) and iii) may have 1 to 4 alkyl radicals $R^1$ to $R^4$ each having 1 to 4 carbon atoms, where one of the radicals $R^1$ to $R^4$ may also be a carboxyl, hydroxymethyl or an alkyloxycarbonyl group having not more than 5 carbon atoms or one or two of the radicals $R^1$ to $R^4$ may be isopropyl, isobutyl, tert-butyl, phenyl or cycloalkyl having 5 to 6 carbon atoms, and where the benzimidazolyl and the (1,2,3,4-tetrahydroisoquinolinyl) fragment in v) and vi) may be unsubstituted or at least monosubstituted.

DETAILED DESCRIPTION

Where groups, fragments, radicals or substituents such as, for example, aryl, heteroaryl, alkyl, alkoxy etc. are present more than once in the compounds of the formula (I), they all have, independently of one another, the meanings listed above and may thus in each (individual) case have either an identical or a mutually independent meaning. The following statements apply to (for example) aryl and every other radical irrespective of whether it is referred to as aryl group, substituent, fragment or radical. A further example is the —N($C_1$-$C_3$-alkyl)$_2$ group in which the two alkyl substituents may be either identical or different (for example twice ethyl or once propyl and once methyl).

Where a substituent, for example aryl, in the above definitions of compounds of the formula (I) may be unsubstituted or at least monosubstituted by a group of further substituents, for example $C_1$-$C_6$-alkyl, $C_1$-$C_6$-alkoxy, halogen etc., the selection from the series of further substituents in the cases where aryl is polysubstituted takes place independently of one another. Thus, for example when aryl is disubstituted, all combinations of the further substituents are included. Aryl may thus be, for example, disubstituted by ethyl, aryl may in each case be monosubstituted by methyl and ethoxy, aryl may in each case be monosubstituted by ethyl and fluorine, aryl may be disubstituted by methoxy etc.

Alkyl radicals may be either linear or branched, acyclic or cyclic. This also applies when they are part of another group such as, for example, alkoxy groups ($C_1$-$C_{10}$-alkyl-O—), alkoxycarbonyl groups or amino groups or if they are substituted.

Examples of alkyl groups are: methyl, ethyl, propyl, butyl, pentyl, hexyl, heptyl, octyl, nonyl or decyl. Included therein are the n-isomers of these radicals and isopropyl, isobutyl, isopentyl, sec-butyl, tert-butyl, neopentyl, 3,3-dimethylbutyl etc. Unless described otherwise, the term alkyl additionally includes alkyl radicals which are unsubstituted or optionally substituted by one or more further radicals, for example 1, 2, 3 or 4 identical or different radicals such as, for example, aryl, heteroaryl, alkoxy or halogen. It is moreover possible for the additional substituents to occur in any position of the alkyl radical. The term alkyl also includes cycloalkyl and cycloalkylalkyl (alkyl which in turn is substituted by cycloalkyl), where cycloalkyl has at least 3 carbon atoms. Cycloalkyl can in turn be substituted by one or more alkyl radicals. Examples of cycloalkyl radicals are: cyclopropyl, cyclobutyl, cyclopentyl, cyclohexyl, cycloheptyl, cyclooctyl, cyclononyl and cyclodecyl. Polycyclic ring systems are also possible where appropriate, such as decalinyl, norbornanyl, bornanyl or adamantanyl. The cycloalkyl radicals may be unsubstituted or optionally substituted by one or more further radicals as listed above by way of example for the alkyl radicals.

Examples of alkenyl and alkynyl groups are: vinyl, 1-propenyl, 2-propenyl (allyl), 2-butenyl, 2-methyl-2-propenyl, 3-methyl-2-butenyl, ethynyl, 2-propynyl (propargyl), 2-butynyl or 3-butynyl. The term alkenyl here expressly includes cycloalkenyl radicals and cycloalkenylalkyl radicals (alkyl substituted by cycloalkenyl) containing at least three carbon atoms. Examples of cycloalkenyl are: cyclopentenyl, cyclohexenyl, cycloheptenyl and cyclooctenyl.

The alkenyl radicals may have one to three conjugated or unconjugated double bonds (i.e. also alk-dienyl and alk-trienyl radicals), preferably one double bond in a linear or branched chain, and the same applies to the triple bonds for alkynyl radicals. The alkenyl and alkynyl radicals may be unsubstituted or optionally substituted by one or more further radicals as listed above by way of example for the alkyl radicals.

Unless stated otherwise, the aforementioned aryl, heteroaryl and heterocyclyl radicals may be both unsubstituted and have one or more, for example 1, 2, 3 or 4 of the aforementioned substituents in any position. For example, the substituent in monosubstituted phenyl radicals may be in position 2, 3 or 4, and the substituents in disubstituted phenyl radicals may be in the 2,3 position, 2,4 position, 2,5 position, 2,6 position, 3,4 position or 3,5 position. The substituents in trisubstituted phenyl radicals may be in the 2,3,4 position, 2,3,5 position, 2,3,6 position, 2,4,5 position, 2,4,6 position or 3,4,5 position. The substituents in tetrasubstituted phenyl radicals may be in the 2,3,4,5 position, the 2,3,4,6 position or in the 2,3,5,6 position.

The definitions mentioned above and hereinafter relating to monovalent radicals apply equally to divalent radicals such as phenylene, naphthylene or heteroarylene. These divalent radicals (fragments) may be linked with the adjacent groups for any ring carbon atom. In the case of phenylene radicals, this may be in the 1,2 position (ortho-phenylene), 1,3 position (meta-phenylene) or 1,4 position (para-phenylene). In the case of a 5-membered aromatic system containing a heteroatom, such as, for example, thiophene or furan, the two free bonds may be in the 2,3 position, 2,4 position, 2,5 position or 3,4 position. A divalent radical derived from a 6-membered aromatic system having one heteroatom, such as, for example, pyridine, may be a 2,3, 2,4, 2,5, 2,6, 3,4 or 3,5 pyridinediyl radical. In the case of unsymmetrical divalent radicals, the present invention also includes all positional isomers, i.e. in the case for example of a 2,3-pyridinediyl radical the compound in which one adjacent group is in position 2 and the other adjacent group is in position 3 is just as much included as the compound in which one adjacent group is in position 3 and the other adjacent group is in position 2.

Unless stated otherwise, heteroaryl radicals, heteroarylene radicals, hetetrocyclyl radicals and heterocyclylene radicals, and rings formed by two groups bonded to nitrogen, are preferably derived from completely saturated, partially or wholly unsaturated heterocycles (i.e. heterocycloalkanes, heterocycloalkenes, heteroaromatic compounds), which contain 1, 2, 3 or 4 heteroatoms which may be both different and identical. They are preferably derived from heterocycles which contain 1, 2 or 3, particularly preferably 1 or 2, heteroatoms which may be identical or different. Unless stated otherwise, the heterocycles are mono- or polycyclic, for example monocyclic, bicyclic or tricyclic. They are preferably monocyclic or bicyclic. Preference is given to 5-membered, 6-membered 7-membered rings, particularly preferably 5-membered and 6-membered rings. In the case of polycyclic heterocycles having 2 or more heteroatoms, these may all be in the same ring or be distributed over a plurality of rings.

Radicals referred to as heteroaryl in the present invention are those derived from monocyclic, bicyclic or tricyclic aromatic heterocycles. Examples of heteroaryl are: pyrrolyl, furanyl (=furyl), thiophenyl (=thienyl), imidazolyl, pyrazolyl, 1,2,3-triazolyl, 1,2,4-triazolyl, 1,3-oxazolyl (=oxazolyl), 1,2-oxazolyl (=isoxazolyl), oxadiazolyl, 1,3-thiazolyl (=thiazolyl), 1,2-thiazolyl (=isothiazolyl), tetrazolyl, pyridinyl (=pyridyl)pyridazinyl, pyrimidinyl, pyrazinyl, 1,2,3-triazinyl, 1,2,4-triazinyl, 1,3,5-triazinyl, 1,2,4,5-tetrazinyl, indazolyl, indolyl, benzothiophenyl, benzofuranyl, benzothiazolyl, benzimidazolyl, quinolinyl, isoquinolinyl, quinazolinyl, quinoxalinyl, phthalazinyl, thienothiophenyl, 1,8-naphthyridinyl, other naphthyridinyls, pteridinyl or thiazolo[3,2-b][1,2,4]-triazolyl. Where the systems are not monocyclic, also included for each of the aforementioned heteroaryls for the second ring is the saturated form (perhydro form) or the partially unsaturated form (for example the dihydro form or tetrahydro form) or the maximally unsaturated (nonaromatic) form where the respective forms are known and stable. The term heteroaryl thus includes in the present invention for example bicyclic radicals in which both the two rings are aromatic and bicyclic radicals in which only one ring is aromatic. Such examples of heteroaryl are: 3H-indolinyl, 2(1H)-quinolinonyl, 4-oxo-1,4-dihydroquinolinyl, 2H-1-oxoisoquinolyl, 1,2-dihydroquinolinyl, 3,4-dihydroquinolinyl, 1,2-dihydroisoquinolinyl, 3,4-dihydroisoquinolinyl, chromonyl, chromanyl, 1,3-benzodioxolyl, oxindolyl, 1,2,3,4-tetrahydroisoquinolinyl, 1,2,3,4-tetrahydroquinolinyl, 5,6-dihydroquinolyl, 5,6-dihydroisoquinolyl, 5,6,7,8-tetrahydroquinolinyl or 5,6,7,8-tetrahydroisoquinolyl.

Radicals referred to as heterocyclyl in the present invention are those derived from monocyclic or bicyclic nonaromatic heterocycles. Nonaromatic heterocycles mean hereinafter in particular heterocycloalkanes (completely saturated heterocycles) and heterocycloalkenes (partially unsaturated heterocycles). In the case of the heterocycloalkenes, also included are compounds having two or more double bonds which may also where appropriate be conjugated together. Examples of heterocyclyl are: pyrrolidinyl, piperidinyl, piperazinyl, imidazolidinyl, pyrazolidinyl, isothiazolidinyl, thiazolidinyl, isoxazolidinyl, oxazolidinyl, tetrahydrofuranyl, tetrahydrothiophenyl, 1,3-dioxolanyl, 1,4-dioxinyl, pyranyl, thiopyranyl, tetrahydro-1,2-oxazinyl, tetrahydro-1,3-oxazinyl, morpholinyl, thiomorpholinyl, 1,2-thiazinyl, 1,3-thiazinyl, 1,4-thiazinyl, azepinyl, 1,2-diazepinyl, 1,3-diazepinyl, 1,4-diazepinyl, 1,3-oxazepinyl, 1,3-thiazepinyl, azepanyl, 2-oxoazepanyl, 1,2,3,4-tetrahydropyridinyl, 1,2-dihydropyridinyl, 1,4-dihydropyridinyl, 1,2,3,6-tetrahydropyridinyl, 4(3H)-pyrimidonyl, 1,4,5,6-tetrahydropyrimidinyl, 2-pyrrolinyl, 3-pyrrolinyl, 2-imidazolinyl, 2-pyrazolinyl, 3,4-dihydro-2H-pyranyl, dihydrofuranyl, 7-oxabicyclo[2.2.1]heptenyl, dihydrothiophenyl and dihydrothiopyranyl. The degree of saturation of heterocyclic groups is indicated in the definition in each case.

Substituents derived from these heterocycles may be linked via any suitable carbon atom, and be provided with further substituents. Radicals derived from nitrogen-containing heterocycles may have a hydrogen atom or another substituent on the appropriate nitrogen atom. Examples include pyrrole, imidazole, pyrrolidine, morpholine, piperazine residues etc. These nitrogen-containing heterocyclic radicals may also be bonded via the ring nitrogen atom, especially when the relevant heterocyclic radical is bonded to a carbon atom. For example, a thienyl radical may be in the form of 2-thienyl or 3-thienyl, and a piperidinyl radical in the form of 1-piperidinyl (piperidino), 2-piperidinyl, 3-piperidinyl or 4-piperidinyl. Suitable nitrogen-containing heterocycles may also be in the form of N-oxides or of quaternary salts which have a counter ion which is derived from a physiologically acceptable acid. For example, pyridyl radicals may be in the form of pyridine N-oxides. Suitable sulfur-containing heterocycles may also be in the form of S-oxide or S,S-dioxide.

Radicals referred to as aryl in the present invention are those derived from monocyclic or bicyclic aromatic systems which contain no ring heteroatoms. Where the systems are not monocyclic, the term aryl for the second ring also encompasses the saturated form (perhydro form) or the partially unsaturated form (for example the dihydro form or tetrahydro form) where the respective forms are known and stable. The term aryl also includes in the present invention for example bicyclic radicals in which both the two rings are aromatic and bicyclic radicals in which only one ring is aromatic. Examples of aryl are: phenyl, naphthyl, indanyl, 1,2-dihydronaphthenyl, 1,4-dihydronaphthenyl, indenyl or 1,2,3,4-tetrahydronaphthyl.

Arylalkyl (such as aryl-($C_1$-$C_6$-alkyl)-) means that an alkyl radical (such as $C_1$-$C_6$-alkyl) is substituted in turn by an aryl radical. Heteroarylalkyl (such as heteroaryl-($C_1$-$C_6$-alkyl)-) means that an alkyl radical (such as $C_1$-$C_6$-alkyl) is substituted in turn by a heteroaryl radical. Heterocyclylalkyl (such as heterocyclyl-($C_1$-$C_6$-alkyl)-) means that an alkyl radical (such as $C_1$-$C_6$-alkyl) is substituted in turn by a heterocyclyl radical. For the definitions and possible substitutions of alkyl, heteroaryl, heterocyclyl and aryl, reference is made to the definitions above.

Halogen is fluorine, chlorine, bromine or iodine, with preference for fluorine, chlorine or bromine, and particular preference for fluorine or chlorine.

The present invention includes all stereoisomeric forms of compounds of the formula (I). Asymmetric carbon atoms in compounds of the formula (I) may have independently of one another S configurations or R configurations. The invention includes all possible enantiomers and diastereomers and mixtures of two or more stereoisomers, for example mixtures of enantiomers and/or diastereomers, in all amounts and ratios. Thus, compounds of the present invention which exist as enantiomers may be in enantiopure form, both as dextrorotatory and as levorotatory antipodes, in the form of racemates and in the form of mixtures of the two enantiomers in all ratios. In the case of cis/trans isomers, the invention includes both the cis form and the trans form as well as mixtures of these forms in all ratios. The present invention relates to all these forms. The individual stereoisomers can be prepared if desired by separating a mixture by conventional methods, for example by chromatography or crystallization, through the use of stereochemically pure starting materials for the synthesis or by stereoselective synthesis. It is also possible alternatively to carry out a derivatization before the separation of the stereoisomers. Separation of a mixture of stereoisomers can be carried out with the compounds of the formula (I) or with the appropriate intermediates during the synthesis. The present invention additionally encompasses all tautomeric forms of compounds of the formula (I), especially keto/enol tautomerism, i.e. the corresponding compounds may be either in their keto form or in their enol form or in mixtures thereof in all ratios.

Where the compounds of the formula (I) comprise one or more acidic or basic groups, the present invention also encompasses the corresponding physiologically or toxicologically acceptable salts.

Physiologically acceptable salts are, because their solubility in water is greater than that of the initial or basic compounds, particularly suitable for medical applications. These salts must have a physiologically acceptable anion or cation. Suitable physiologically acceptable acid addition salts of the compounds of the invention are salts of inorganic acids such as hydrochloric acid, hydrobromic, phosphoric, metaphosphoric, nitric, sulfonic and sulfuric acids, and of organic acids such as, for example, acetic acid, theophyllineacetic acid, methylenebis-b-oxynaphthonic, benzenesulfonic, benzoic, citric, ethanesulfonic, salicylic, fumaric, gluconic, glycolic, isethionic, lactic, lactobionic, maleic, malic, methanesulfonic, succinic, p-toluenesulfonic, tartaric and trifluoroacetic acids. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise belong within the framework of the invention as useful intermediates for preparing or purifying pharmaceutically acceptable salts and/or for use in non-therapeutic, for example in vitro applications.

Where compounds of the formula (I) comprise both acidic and basic groups in the same molecule, the present invention includes—in addition to the salt forms detailed previously—also inner salts or betaines (zwifterions).

The corresponding salts of the compounds of the formula (I) can be obtained by conventional methods known to the skilled worker, for example by reacting with an organic or inorganic acid or base in a solvent or dispersant, or by anion or cation exchange with other salts.

The present invention additionally includes all solvates of compounds of the formula (I), for example hydrates or adducts with alcohol, active metabolites of compounds of the formula (I), and derivatives which comprise a physiologically acceptable group which can be eliminated, for example esters or amides.

The term "physiologically functional derivative" used herein refers to any physiologically acceptable derivative of a compound of the invention of the formula I, e.g. an ester which, on administration to a mammal such as, for example, a human, is able (directly or indirectly) to form a compound of the formula I or an active metabolite thereof.

The physiologically functional derivatives also include prodrugs of the compounds of the invention. Such prodrugs may be metabolized in vivo to a compound of the invention. These prodrugs may themselves be active or inactive, and the present invention likewise relates thereto.

The compounds of the invention may also exist in various polymorphous forms, e.g. as amorphous and crystalline polymorphous forms. All polymorphous forms of the compounds of the invention are included within the framework of the invention and are a further aspect of the invention.

Compounds of the formula (I) having the following meanings are preferred:

R1 is hydrogen, halogen or —$CF_3$;

R2 is hydrogen, —$NH_2$, —$NH(C_1$-$C_3$-alkyl), —$N(C_1$-$C_3$-alkyl)$_2$ or $C_1$-$C_3$-alkoxy and R1 and R2 may not simultaneously be hydrogen;

R3 is unsubstituted or at least monosubstituted $C_1$-$C_{10}$-alkyl, $C_2$-$C_{10}$-alkenyl, aryl or heterocyclyl, where the substituents are selected from the group consisting of:

aryl, heteroaryl, heterocyclyl, aryl-($C_1$-$C_6$-alkyl)-, heterocyclyl-($C_1$-$C_6$-alkyl)-, heteroaryl-($C_1$-$C_6$-alkyl)-, —O-aryl, fluorine, chlorine, bromine, —$CF_3$, —$OCF_3$, —$NO_2$, —CN, —C(O)R7, hydroxy, $C_1$-$C_6$-alkyl and $C_1$-$C_3$-alkoxy, and the aryl, heteroaryl and heterocyclyl fragments of these substituents may in turn be at least monosubstituted by fluorine, chlorine, bromine, oxo, —$CF_3$, —$OCF_3$, —$NO_2$, —CN, hydroxy, $C_1$-$C_3$-alkyl or $C_1$-$C_3$-alkoxy;

R4 and R5 are independently of one another hydrogen, unsubstituted or at least monosubstituted $C_1$-$C_{10}$-alkyl, where the substituents are selected from:

halogen, $C_1$-$C_6$-alkoxy, —$CF_3$ or hydroxy; or

R4 and R5 form together with the nitrogen atom to which they are bonded unsubstituted or at least monosubstituted heterocyclyl, where the substituents are selected from:

halogen, $C_1$-$C_6$-alkyl, $C_1$-$C_6$-alkoxy, —$CF_3$ or hydroxy;

R6 is hydrogen, —$SO_2(C_1$-$C_3$-alkyl), unsubstituted or at least monosubstituted $C_1$-$C_{10}$-alkyl, $C_2$-$C_{10}$-alkenyl or aryl-($C_1$-$C_6$-alkyl)-, where the substituents are selected from:

halogen, $C_1$-$C_6$-alkyl, $C_1$-$C_6$-alkoxy, —$CF_3$ or hydroxy; or

R6 forms together with R3 and X, if X is equal to N, unsubstituted or at least monosubstituted heterocyclyl, where the substituents are selected from the group consisting of:

aryl, heteroaryl, heterocyclyl, aryl-($C_1$-$C_6$-alkyl)-, heterocyclyl-($C_1$-$C_6$-alkyl)-, heteroaryl-($C_1$-$C_6$-alkyl)-, —O-aryl, fluorine, chlorine, bromine, —$CF_3$, —$OCF_3$, —$NO_2$, —CN, —C(O)R7, hydroxy, $C_1$-$C_6$-alkyl and $C_1$-$C_3$-alkoxy, and the aryl, heteroaryl and heterocyclyl fragments of these substituents may in turn be at least monosubstituted by fluorine, chlorine, bromine, oxo, —$CF_3$, —$OCF_3$, —$NO_2$, —CN, hydroxy, $C_1$-$C_3$-alkyl or $C_1$-$C_3$-alkoxy;

R7 is $C_1$-$C_3$-alkoxy, —O-phenyl, $C_1$-$C_3$-alkyl, —$NH_2$, —NH($C_1$-$C_3$-alkyl), —$N(C_1$-$C_3$-alkyl)$_2$ or phenyl, and the phenyl fragments of R7 may in turn be at least monosubstituted by fluorine, chlorine, bromine, —$CF_3$, —$OCF_3$, —$NO_2$, —CN, hydroxy, $C_1$-$C_3$-alkyl or $C_1$-$C_3$-alkoxy;

A is $SO_2$, CO or $CH_2$;

X is NR6 or O;

heteroaryl is a 5 to 10-membered, aromatic, mono- or bicyclic heterocycle which comprises one or more heteroatoms selected from N, O and S; heteroaryl is preferably pyridinyl, thienyl, pyrimidinyl, imidazolyl, furanyl, benzimidazolyl, pyrazolyl, thiazolyl, isoxazolyl, pyrrolyl, pyrazinyl, 3-oxo-1,3-dihydroisobenzofuranyl or 4,5,6,7-tetrahydrobenzothiazolyl; heteroaryl is particularly preferably pyridinyl, thienyl, pyrazolyl, furanyl or benzimidazolyl;

aryl is a 5 to 10-membered aromatic, mono- or bicyclic system; aryl is preferably phenyl, indanyl or naphthyl; aryl is particularly preferably phenyl;

heterocyclyl is a 5 to 10-membered, nonaromatic, mono- or bicyclic heterocycle which comprises one or more heteroatoms selected from N, O and S; heterocyclyl is preferably morpholinyl, pyrrolidinyl, piperidinyl, tetrahydropyranyl, thiazolidinyl, dihydroisoxazolyl, piperazinyl or tetrahydrofuranyl; heterocyclyl is particularly preferably morpholinyl, pyrrolidinyl, piperidinyl or piperazinyl;

or a physiologically acceptable salt thereof.

More preferred compounds of the formula (I) have the following meanings:

R1 is hydrogen, halogen or —$CF_3$;

R2 is hydrogen, —$NH_2$, —$NH(C_1$-$C_3$-alkyl), —$N(C_1$-$C_3$-alkyl)$_2$ or $C_1$-$C_3$-alkoxy and R1 and R2 may not both be hydrogen;

R3 is unsubstituted or at least monosubstituted $C_1$-$C_{10}$-alkyl, $C_2$-$C_6$-alkenyl, aryl or heterocyclyl, where the substituents are selected from the group consisting of:

aryl, aryl-($C_1$-$C_6$-alkyl)-, fluorine, chlorine, bromine, —$CF_3$, —C(O)O—($C_1$-$C_3$-alkyl), —C(O)O-phenyl, hydroxy, $C_1$-$C_3$-alkyl and $C_1$-$C_3$-alkoxy, and the aryl fragments of these substituents may in turn be at least monosubstituted by fluorine, chlorine, bromine, oxo, —$CF_3$, hydroxy, $C_1$-$C_3$-alkyl or $C_1$-$C_3$-alkoxy;

R4 and R5 are independently of one another hydrogen, unsubstituted or at least monosubstituted $C_1$-$C_{10}$-alkyl, where the substituents are selected from:

halogen, $C_1$-$C_6$-alkoxy, —$CF_3$ or hydroxy or

R4 and R5 form together with the nitrogen atom to which they are bonded unsubstituted or at least monosubstituted heterocyclyl, where the substituents are selected from:
halogen, $C_1$-$C_6$-alkyl, $C_1$-$C_6$-alkoxy, —$CF_3$ or hydroxy;
R6 is hydrogen, —$SO_2$($C_1$-$C_3$-alkyl), unsubstituted or at least monosubstituted $C_1$-$C_{10}$-alkyl or $C_2$-$C_6$-alkenyl,
where the substituents are selected from:
halogen, $C_1$-$C_6$-alkoxy or —$CF_3$; or
R6 forms together with R3 and X, if X is equal to N, unsubstituted or at least monosubstituted heterocyclyl,
where the substituents are selected from the group consisting of:
aryl, aryl-($C_1$-$C_6$-alkyl)-, fluorine, chlorine, bromine, —$CF_3$, —C(O)O—($C_1$-$C_3$-alkyl), —C(O)O-phenyl, hydroxy, $C_1$-$C_3$-alkyl and $C_1$-$C_3$-alkoxy,
and the aryl fragments of these substituents may in turn be at least monosubstituted by fluorine, chlorine, bromine, oxo, —$CF_3$, hydroxy, $C_1$-$C_3$-alkyl or $C_1$-$C_3$-alkoxy;
A is $SO_2$, CO or $CH_2$;
X is NR6 or O;
aryl is phenyl, indanyl or naphthyl; aryl is particularly preferably phenyl;
heterocyclyl is morpholinyl, pyrrolidinyl, piperidinyl, tetrahydropyranyl, thiazolidinyl, dihydroisoxazolyl, piperazinyl or tetrahydrofuranyl; heterocyclyl is particularly preferably morpholinyl, pyrrolidinyl, piperidinyl or piperazinyl;
or a physiologically acceptable salt thereof.

Even more preferred compounds of the formula (I) have the following meanings:
R1 is chlorine, fluorine or —$CF_3$;
R2 is hydrogen, —$NH_2$ or $C_1$-$C_3$-alkoxy;
R3 is unsubstituted or at least monosubstituted $C_1$-$C_{10}$-alkyl, $C_2$-$C_6$-alkenyl, phenyl or heterocyclyl,
where the substituents are selected from the group consisting of:
phenyl, phenyl-($C_1$-$C_6$-alkyl)-, fluorine, chlorine, bromine, —$CF_3$, —C(O)O—($C_1$-$C_3$-alkyl), hydroxy, $C_1$-$C_3$-alkyl and $C_1$-$C_3$-alkoxy,
and the phenyl fragments of these substituents may in turn be at least monosubstituted by fluorine, chlorine, bromine, oxo, —$CF_3$, hydroxy, $C_1$-$C_3$-alkyl or $C_1$-$C_3$-alkoxy;
R4 and R5 are independently of one another $C_1$-$C_6$-alkyl; or
R4 and R5 form together with the nitrogen atom to which they are bonded unsubstituted or at least monosubstituted heterocyclyl,
where the substituents are selected from:
halogen, $C_1$-$C_6$-alkyl, $C_1$-$C_6$-alkoxy, —$CF_3$ or hydroxy;
R6 is hydrogen, —$SO_2$($C_1$-$C_3$-alkyl), unsubstituted or at least monosubstituted $C_1$-$C_6$-alkyl or $C_2$-$C_3$-alkenyl,
where the substituents are selected from:
halogen, $C_1$-$C_6$-alkoxy or —$CF_3$; or
R6 forms together with R3 and X, if X is equal to N, unsubstituted or at least monosubstituted heterocyclyl,
where the substituents are selected from the group consisting of:
phenyl, phenyl-($C_1$-$C_6$-alkyl)-, fluorine, chlorine, bromine, —$CF_3$, —C(O)O—($C_1$-$C_3$-alkyl), hydroxy, $C_1$-$C_3$-alkyl and $C_1$-$C_3$-alkoxy,
and the phenyl fragments of these substituents may in turn be at least monosubstituted by fluorine, chlorine, bromine, oxo, —$CF_3$, hydroxy, $C_1$-$C_3$-alkyl or $C_1$-$C_3$-alkoxy;
A is $SO_2$, CO or $CH_2$;
X is NR6 or O;
heterocyclyl is morpholinyl, pyrrolidinyl, piperidinyl or piperazinyl;
or a physiologically acceptable salt thereof.

Much more preferred compounds of the formula (I) have the following meanings:
R1 is chlorine or —$CF_3$;
R2 is hydrogen or —$NH_2$;
R3 is unsubstituted or at least monosubstituted $C_1$-$C_6$-alkyl, $C_2$-$C_3$-alkenyl or phenyl,
where the substituents are selected from: $C_1$-$C_3$-alkyl, $C_1$-$C_3$-alkoxy, chlorine, fluorine or hydroxy;
R4 and R5 are each methyl;
R6 is hydrogen, —$SO_2CH_3$ or $C_1$-$C_6$-alkyl;
A is $SO_2$ or $CH_2$;
X is NR6 or O;
or a physiologically acceptable salt thereof.

Particularly preferred compounds of the formula (I) are selected from the group consisting of:
6-chloro-N-dimethylaminomethylene-3-[(3,5-dimethylphenoxy)methyl]benzenesulfonamide; 6-chloro-N-dimethylaminomethylene-3-[(N-(3,3,5-trimethylcyclohexyl)-N-methylsulfonylamino)methyl]benzenesulfonamide; 6-chloro-N-dimethylaminomethylene-3-(3,3,5-trimethylcyclohexylaminosulfonyl)benzenesulfonamide; 2-amino-4-chloro-5-dimethylaminomethylenesulfamoyl-N-dibutylbenzenesulfonamide; 2-amino-4-chloro-5-dimethylaminomethylenesulfamoyl-N-diisobutylbenzenesulfonamide; 2-amino-4-chloro-5-dimethylaminomethylenesulfamoyl-N-(3,3,5-trimethylcyclohexyl)benzenesulfonamide; 2-amino-4-chloro-5-dimethylaminomethylenesulfamoyl-N-cyclohexyl-N-allyl-benzenesulfonamide and 2-amino-4-trifluoromethyl-5-dimethylaminomethylenesulfamoyl-N-cyclohexylbenzenesulfonamide.

The compounds of the formula I can be prepared by various chemical processes which likewise form part of the present invention. Some typical routes are detailed below, with all the substituents (R, A and X) being defined as indicated above unless stated otherwise hereinafter. The starting compounds and the intermediates are either commercially available or can be prepared by processes known to the skilled worker.

A customary method for preparing N-aminomethylene compounds of the formula I consists of reacting the sulfonamides II with dialkylformamide acetals in a suitable solvent such as, for example, DMF, toluene or chlorobenzene. This reaction can also be carried out analogously when the —A—X—R3 fragment in the formula (II) is replaced by an —A—Z fragment according to formula (III) below. The intermediate obtained in this way corresponds to a compound of the following formula (III).

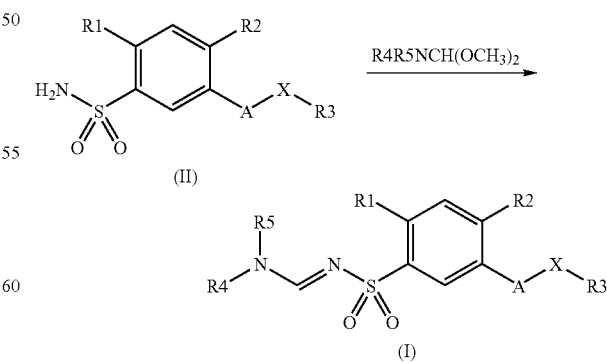

A further possibility consists of the introduction (exchange) of the R4R5N group by heating compounds of the general structure 1 in which R4 and R5 is methyl with amines of the general structure R4R5NH, either without or with a suitable inert solvent such as, for example, toluene, chlorobenzene, ethanol, isopropanol, butanol.

The radical A—X—R3 may be SO$_2$—NR3R6 and can be obtained starting from chlorosulfonyl compounds by reaction with amines of the general formula HNR3R6. The halogen compounds of the formula III can very generally be converted into the compounds of the formula I by reactions with the nucleophiles HXR3. This reaction can also be carried out analogously if the —SO$_2$—N=CH—NR4R5 fragment in the formula (III) is replaced by an —SO$_2$—NH$_2$ fragment. The intermediate obtained in this way corresponds to a compound of the formula (II).

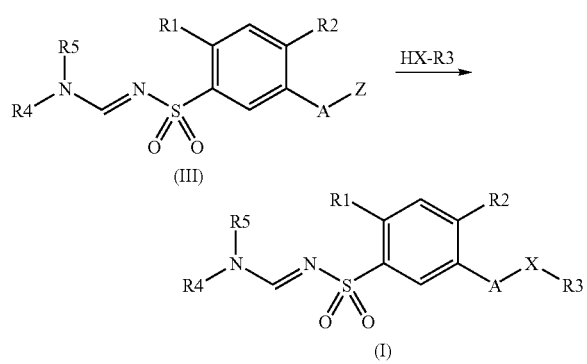

In this case, A—Z is, for example, COCl, SO$_2$Cl, SO$_2$F, CH$_2$Cl or CH$_2$Br and HX-R3 is for example primary and secondary amines, alcohols or phenols.

These reactions take place in a known manner in inert solvents at 0-100° C., preferably in the presence of auxiliary bases which are able to bind the hydrogen halide formed.

The compounds of the formula III can be obtained in a manner known per se by halogenation of the corresponding carboxylic acids (—COOH), alcohols (—CH$_2$OH) or sulfonic acids (—SO$_3$H) or by sulfochlorination with chlorosulfonic acids starting from known precursors as are described for example in J. Med. Chem. 29, 1814-20 (1986) or in DE 2109339.

It may be appropriate in all the procedures for functional groups in the molecule to be protected temporarily in certain reaction protocols. Such protective groups are familiar to the skilled worker. Selection of a protective group for groups which come into consideration, and the processes for their introduction and elimination are described in the literature and can be adapted where appropriate for the individual case without difficulty.

The present invention also relates to the use of compounds of the general formula (I) as pharmaceutical or medicament. Concerning the definitions of the substituents R1 to R5 (and of the other substituents defined via the aforementioned substituents), A and X, reference is made to the statements concerning the compound as such.

The use of compounds of the formula (I) as pharmaceuticals, where the compounds have the abovementioned preferred, more preferred, even more preferred, much more preferred or particularly preferred meanings is also an aspect of the present invention.

The compounds of the invention of the formula (I) have a surprising inhibitory effect on hormone-sensitive lipase, HSL, an allosteric enzyme in adipocytes which is inhibited by insulin and is responsible for the breakdown of fats in adipose cells and thus for transferring constituents of fats into the bloodstream. Thus, inhibition of this enzyme corresponds to an insulin-like effect of the compounds of the invention, which finally leads to a reduction in free fatty acids in the blood, and in blood glucose. They can thus be employed for metabolic derangements such as, for example, for non-insulin-dependent diabetes mellitus (type II diabetes mellitus), for the diabetic syndrome and for obesity. The treatment of type II diabetes mellitus is preferred. The compounds of the invention of the formula (I) are additionally suitable as inhibitor of monoacylglyceride lipase.

The term treatment in the above statements also includes the prophylaxis, therapy or cure of the aforementioned diseases.

All references to "compound(s) of the formula (I)" hereinafter refer to compound(s) of the formula (I) as described above, and their salts, solvates and physiologically functional derivatives as described herein.

The compounds of the formula (I) can be administered to animals and humans, preferably mammals and humans, particularly preferably humans. The compounds of the formula (I) can in this connection be administered themselves as pharmaceutical, in mixtures with one another or in mixtures with other pharmaceuticals or in the form of pharmaceutical compositions. Consequently, the use of compounds of the formula (I) for producing one or more medicaments for the prophylaxis and/or treatment of the aforementioned diseases, pharmaceutical compositions comprising an effective amount of at least one compound of the formula (I), and pharmaceutical compositions comprising an effective amount of at least one compound of the formula (I) for the prophylaxis and/or treatment of the aforementioned diseases are likewise aspects of the present invention.

The amount of a compound of the formula (I) which is necessary in order to achieve the desired biological effect depends on a number of factors, e.g. the specific compound chosen, the intended use, the mode of administration and the clinical condition of the patient. The daily dose is generally in the range from 0.3 mg to 100 mg (typically from 3 mg to 50 mg) per day per kilogram of body weight, e.g. 3-10 mg/kg/day. An intravenous dose may be for example in the range from 0.3 mg to 1.0 mg/kg, which can suitably be administered as infusion of from 10 ng to 100 ng per kilogram per minute. Suitable infusion solutions for these purposes may comprise for example from 0.1 ng to 10 mg, typically from 1 ng to 10 mg, per milliliter. Single doses may comprise for example from 1 mg to 10 g of the active ingredient. Thus, ampoules for injections may comprise for example from 1 mg to 100 mg, and single-dose formulations which can be administered orally, such as, for example, tablets or capsules, may comprise for example from 1.0 to 1000 mg, typically from 10 to 600 mg. In the case of pharmaceutically acceptable salts, the aforementioned weight data refer to the weight of the free compound from which the salt is derived. For the prophylaxis or therapy of the abovementioned conditions it is possible for the compounds of the formula (I) to be used themselves as compound, but they are preferably present together with an acceptable carrier in the form of a pharmaceutical composition. The carrier must, of course, be acceptable in the sense that it is compatible with the other ingredients of the composition and is not harmful for the patient's health (physiologically acceptable). The carrier may be a solid or a liquid or both and is preferably formulated with the compound as single dose, for example as tablet which may comprise from 0.05% to 95% by weight of the active ingredient. Further pharmaceutically active substances may likewise be present, including further compounds of the formula (I). The pharmaceutical compositions of the invention can be produced by one of the known pharmaceutical methods, which essentially consist of mixing the ingredients with pharmacologically acceptable carriers and/or excipients.

Besides at least one compound of the formula (I) and one or more carriers, the pharmaceutical compositions of the invention may also comprise excipients. Examples of suitable excipients or additives are: fillers, binders, lubricants, wetting agents, stabilizers, emulsifiers, dispersants, preservatives, sweeteners, colorants, flavorings, aromatizing substances, thickeners, diluents, buffer substances, solvents, solubilizers, agents with which a depot effect can be achieved, salts to alter the osmotic pressure, coating agents or antioxidants.

The pharmaceutical compositions of the invention may for example be in the form of a pill, tablet, coated tablet, suckable tablet, granules, capsule, hard or soft gelatin capsule, aqueous solution, alcoholic solution, oily solution, syrup, emulsion, suspension, suppository, pastille, solution for injection or infusion, ointment, tincture, cream, lotion, dusting powder, spray, transdermal therapeutic system, nasal spray, aerosol, aerosol mixture, microcapsule, implant, rod or patch.

Pharmaceutical compositions of the invention are those suitable for oral, rectal, topical, peroral (for example sublingual) and parenteral (e.g. subcutaneous, intramuscular, intradermal or intravenous) administration, although the most suitable mode of administration depends in each individual case on the nature and severity of the condition to be treated and on the nature of the compound of formula (I) used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, suckable tablets or tablets, each of which contain a defined amount of the compound of formula (I); in the form of powders (gelatin capsules or sachets) or granules; as solution or suspension in an aqueous or nonaqueous liquid; or in the form of an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, lubricant, inert diluent and/or one (or more) surface-active/dispersing agent(s) in a suitable machine. Molded tablets can be produced by molding the compound, which is in powder form and is moistened with an inert liquid diluent, in a suitable machine. Examples of suitable diluents are starch, cellulose, sucrose, lactose or silica gel. The pharmaceutical compositions of the invention may additionally comprise substances which are not diluents, for example one or more lubricants such as magnesium stearate or talc, a colorant, a coating (coated tablets) or a lacquer.

Pharmaceutical compositions which are suitable for peroral (sublingual) administration comprise suckable tablets which contain a compound of formula (I) with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of a compound of the formula (I), which are preferably isotonic with the blood of the intended recipient. These preparations are preferably administered intravenously, although administration can also take place by subcutaneous, intramuscular or intradermal injection. These preparations can preferably be produced by mixing the compound with water, and making the resulting solution sterile and isotonic with blood. Injectable compositions of the invention generally comprise from 0.1 to 5% by weight of the active compound.

The sterile compositions for parenteral administration may preferably be aqueous or nonaqueous solutions, suspensions or emulsions. Solvents or vehicles which can be used are water, propylene glycol, polyethylene glycol and vegetable oils, especially olive oil, organic esters for injection, for example ethyl oleate, or other suitable organic solvents. These compositions may also comprise adjuvants, especially wetting agents, agents for adjusting isotonicity, emulsifiers, dispersants and stabilizers. Sterilization can take place in several ways, for example by aseptic filtration, by introducing sterilizing agents into the composition, by irradiation or by heating. The compositions may also be produced in the form of sterile solid compositions which on use are dissolved in sterile water or another sterile injection medium.

Pharmaceutical compositions suitable for rectal administration are preferably in the form of single-dose suppositories. These can be produced by mixing a compound of the formula (I) with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an optionally buffered aqueous solution, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described for example in Pharmaceutical Research, 2(6): 318 (1986).

Combinations with Other Medicaments

The compounds of the invention can be administered alone or in combination with one or more further pharmacologically active substances which have, for example, favorable effects on metabolic disturbances or disorders frequently associated therewith. Examples of such medicaments are 1. medicaments which lower blood glucose, antidiabetics,
2. active ingredients for the treatment of dyslipidemias,
3. antiatherosclerotic medicaments,
4. antiobesity agents,
5. antiinflammatory active ingredients
6. active ingredients for the treatment of malignant tumors
7. antithrombotic active ingredients 8. active ingredients for the treatment of high blood pressure
9. active ingredients for the treatment of heart failure and
10. active ingredients for the treatment and/or prevention of complications caused by diabetes or associated with diabetes.

They can be combined with the compounds of the invention of the formula (I) in particular for a synergistic improvement in the effect. Administration of the active ingredient combination can take place either by separate administration of the active ingredients to the patient or in the form of combination products in which a plurality of active ingredients are present in one pharmaceutical preparation.

Examples which may be mentioned are:

Antidiabetics

Suitable antidiabetics are disclosed for example in the Rote Liste 2001, chapter 12 or in the USP Dictionary of USAN and International Drug Names, US Pharmacopoeia, Rockville 2003. Antidiabetics include all insulins and insulin derivatives such as, for example, Lantus® (see www.lantus.com) or Apidra®, and other fast-acting insulins (see U.S. Pat. No. 6,221,633), GLP-1 receptor modulators as described in WO 01/04146 or else, for example, those disclosed in WO 98/08871 of Novo Nordisk A/S.

The orally effective hypoglycemic active ingredients include, preferably, sulfonylureas, biguanides, meglitinides, oxadiazolidinediones, thiazolidinediones, glucosidase inhibitors, glucagon antagonists, oral GLP-1 agonists, DPP-IV inhibitors, potassium channel openers such as, for example, those disclosed in WO 97/26265 and WO 99/03861, insulin sensitizers, inhibitors of liver enzymes involved in the stimulation of gluconeogenesis and/or glycogenolysis, modulators of glucose uptake, compounds which alter lipid metabolism and lead to a change in the blood lipid composition, compounds which reduce food intake or food absorption, PPAR and PXR modulators and active ingredients which act on the ATP-dependent potassium channel of the beta cells.

In one embodiment of the invention, the compounds of the formula (I) are administered in combination with insulin.

In one embodiment of the invention, the compounds of the formula (I) are administered in combination with substances which influence hepatic glucose production, such as, for example, glycogen phosphorylase inhibitors (see: WO 01/94300, WO 02/096864, WO 03/084923, WO 03/084922, WO 03/104188).

In one embodiment, the compounds of the formula (I) are administered in combination with a sulfonylurea such as, for example, tolbutamide, glibenclamide, glipizide or glimepiride.

In one embodiment, the compounds of the formula (I) are administered in combination with an active ingredient which acts on the ATP-dependent potassium channel of the beta cells, such as, for example, tolbutamide, glibenclamide, glipizide, glimepiride or repaglinide.

In one embodiment, the compounds of the formula (I) are administered in combination with a biguanide such as, for example, metformin.

In a further embodiment, the compounds of the formula (I) are administered in combination with a meglitinide such as, for example, repaglinide.

In one embodiment, the compounds of the formula (I) are administered in combination with a thiazolidinedione such as, for example, ciglitazone, pioglitazone, rosiglitazone or the compounds disclosed in WO 97/41097 of Dr. Reddy's Research Foundation, in particular 5-[[4-[(3,4-dihydro-3-methyl-4-oxo-2-quinazolinylmethoxy]phenyl]methyl]-2,4-thiazolidinedione.

In one embodiment, the compounds of the formula (I) are administered in combination with a DPPIV inhibitor as described, for example, in WO98/19998, WO99/61431, WO99/67278, WO99/67279, WO01/72290, WO 02/38541, WO03/040174, in particular P 93/01 (1-cyclopentyl-3-methyl-1-oxo-2-pentanammonium chloride), P-31/98, LAF237 (1-[2-[3-hydroxyadamant-1-ylamino)acetyl]pyrrolidine-2-(S)-carbonitrile), TS021 ((2S,4S)-4-fluoro-1-[[(2-hydroxy-1,1-dimethylethyl)amino]acetyl]pyrrolidine-2-carbonitrile monobenzenesulfonate).

In one embodiment of the invention, the compounds of the formula (I) are administered in combination with a PPAR-gamma agonist such as, for example, rosiglitazone, pioglitazone.

In one embodiment, the compounds of the formula (I) are administered in combination with compounds with an inhibitory effect on SGLT-1 and/or 2, as disclosed directly or indirectly for example in PCT/EP03/06841, PCT/EP03/13454 and PCT/EP03/13455.

In one embodiment, the compounds of the formula (I) are administered in combination with an α-glucosidase inhibitor such as, for example, miglitol or acarbose.

In one embodiment, the compounds of the formula (I) are administered in combination with more than one of the aforementioned compounds, e.g. in combination with a sulfonylurea and metformin, a sulfonylurea and acarbose, repaglinide and metformin, insulin and a sulfonylurea, insulin and metformin, insulin and troglitazone, insulin and lovastatin, etc.

Lipid Modulators

In one embodiment of the invention, the compounds of the formula (I) are administered in combination with an HMG-CoA reductase inhibitor such as lovastatin, fluvastatin, pravastatin, simvastatin, ivastatin, itavastatin, atorvastatin, rosuvastatin.

In one embodiment of the invention, the compounds of the formula (I) are administered in combination with a bile acid absorption inhibitor (see, for example, U.S. Pat. No. 6,245,744, 6,221,897, 6,277,831, EP 0683 773, EP 0683 774).

In one embodiment of the invention, the compounds of the formula (I) are administered in combination with a polymeric bile acid adsorbent such as, for example, cholestyramine, colesevelam.

In one embodiment of the invention, the compounds of the formula (I) are administered in combination with a cholesterol absorption inhibitor as described for example in WO 0250027, or ezetimibe, tiqueside, pamaqueside.

In one embodiment of the invention, the compounds of the formula (I) are administered in combination with an LDL receptor inducer (see, for example, U.S. Pat. No. 6,342,512).

In one embodiment, the compounds of the formula (I) are administered in combination with bulking agents, preferably insoluble bulking agents (see, for example, carob/Caromax® (Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, Industriepark Höchst, 65926 Frankfurt/Main)). Combination with Caromax® is possible in one preparation or by separate administration of compounds of the formula (I) and Caromax®. Caromax® can in this connection also be administered in the form of food products such as, for example, in bakery products or muesli bars.

In one embodiment of the invention, the compounds of the formula (I) are administered in combination with a PPARalpha agonist.

In one embodiment of the invention, the compounds of the formula (I) are administered in combination with a fibrate such as, for example, fenofibrate, gemfibrozil, clofibrate, bezafibrate.

In one embodiment of the invention, the compounds of the formula (I) are administered in combination with nicotinic acid or niacin.

In one embodiment of the invention, the compounds of the formula (I) are administered in combination with a CETP inhibitor, e.g. CP-529, 414 (torcetrapib).

In one embodiment of the invention, the compounds of the formula (I) are administered in combination with an ACAT inhibitor.

In one embodiment of the invention, the compounds of the formula (I) are administered in combination with an MTP inhibitor such as, for example, implitapide.

In one embodiment of the invention, the compounds of the formula (I) are administered in combination with an antioxidant.

In one embodiment of the invention, the compounds of the formula (I) are administered in combination with a lipoprotein lipase inhibitor.

In one embodiment of the invention, the compounds of the formula (I) are administered in combination with an ATP citrate lyase inhibitor.

In one embodiment of the invention, the compounds of the formula (I) are administered in combination with a squalene syntheses inhibitor.

In one embodiment of the invention, the compounds of the formula (I) are administered in combination with a lipoprotein (a) antagonist.

Antiobesity Agents

In one embodiment of the invention, the compounds of the formula (I) are administered in combination with a lipase inhibitor such as, for example, orlistat.

In one embodiment, the further active ingredient is fenfluramine or dexfenfluramine.

In another embodiment, the further active ingredient is sibutramine. In a further embodiment, the compounds of the formula (I) are administered in combination with CART modulators (see "Cocaine-amphetamine-regulated transcript influences energy metabolism, anxiety and gastric emptying in mice" Asakawa, A, et al., M.: Hormone and Metabolic Research (2001), 33(9), 554-558), NPY antagonists, e.g. naphthalene-1-sulfonic acid {4-[(4-aminoquinazolin-2-ylamino)methyl]cyclohexylmethyl}amide hydrochloride (CGP 71683A)), MC4 agonists (e.g. 1-amino-1,2,3,4-tetrahydronaphthalene-2-carboxylic acid [2-(3a-benzyl-2-methyl-3-oxo-2,3,3a,4,6,7-hexahydropyrazolo[4,3-c]pyridin-5-yl)-1-(4-chlorophenyl)-2-oxoethyl]amide; (WO 01/91752)), orexin antagonists (e.g. 1-(2-methylbenzoxazol-6-yl)-3-[1,5]naphthyridin-4-ylurea hydrochloride (SB-334867-A)), H3 agonists (3-cyclohexyl-1-(4,4-dimethyl-1,4,6,7-tetrahydroimidazo-[4,5-c]pyridin-5-yl)propan-1-one oxalic acid salt (WO 00/63208)); TNF agonists, CRF antagonists (e.g. [2-methyl-9-(2,4,6-trimethylphenyl)-9H-1,3,9-triazafluoren-4-yl]dipropylamine (WO 00/66585)), CRF BP antagonists (e.g. urocortin), urocortin agonists, β3 agonists (e.g. 1-(4-chloro-3-methanesulfonylmethylphenyl)-2-[2-(2,3-dimethyl-1H-indol-6-yloxy)ethylamino]ethanol hydrochloride (WO 01/83451)), MSH (melanocyte-stimulating hormone) agonists, CCK-A agonists (e.g. {2-[4-(4-chloro-2,5-dimethoxyphenyl)-5-(2-cyclohexylethyl)thiazol-2-ylcarbamoyl]-5,7-di-methylindol-1-yl}acetic acid trifluoroacetic acid salt (WO 99/15525)), serotonin reuptake inhibitors (e.g. dexfenfluramine), mixed serotoninergic and noradrenergic compounds (e.g. WO 00/71549), 5HT agonists e.g. 1-(3-ethylbenzofuran-7-yl)piperazine oxalic acid salt (WO 01/09111), bombesin agonists, galanin antagonists, growth hormone (e.g. human growth hormone), growth hormone-releasing compounds (6-benzyloxy-1-(2-diisopropylaminoethylcarbamoyl)-3,4-dihydro-1H-isoquinoline-2-carboxylic acid tertiary butyl ester (WO 01/85695)), TRH agonists (see, for example, EP 0 462 884), uncoupling protein 2 or 3 modulators, leptin agonists (see, for example, Lee, Daniel W.; Leinung, Matthew C.; Rozhavskaya-Arena, Marina; Grasso, Patricia. Leptin agonists as a potential approach to the treatment of obesity. Drugs of the Future (2001), 26(9), 873-881), DA agonists (bromocriptine, Doprexin), lipase/amylase inhibitors (e.g. WO 00/40569), PPAR modulators (e.g. WO 00/78312), RXR modulators or TR-β agonists.

In one embodiment of the invention, the further active ingredient is leptin.

In one embodiment, the further active ingredient is dexamphetamine, amphetamine, mazindole or phentermine.

In one embodiment, the compounds of the formula (I) are administered in combination with medicaments having effects on the coronary circulation and the vascular system, such as, for example, ACE inhibitors (e.g. ramipril), medicaments which act on the angiotensin-renin system, calcium antagonists, beta blockers etc.

In one embodiment, the compounds of the formula (I) are administered in combination with medicaments having an antiinflammatory effect.

In one embodiment, the compounds of the formula (I) are administered in combination with medicaments which are employed for cancer therapy and cancer prevention.

It will be appreciated that every suitable combination of the compounds of the invention with one or more of the aforementioned compounds and optionally one or more other pharmacologically active substances is regarded as falling within the protection conferred by the present invention.

EXPERIMENTAL SECTION

The following examples describe the invention in more detail without restricting it.

EXAMPLES

Example 1

4-Methoxy-3-hydroxymethyl-N-dimethylaminomethylenephenylsulfonamide

The mixture consisting of 1 g of 4-methoxy-3-hydroxymethylphenylsulfonamide, 0.66 g of dimethylformamide dimethyl acetal and 5 ml of dimethylformamide is stirred at 80° C. for one hour and then concentrated in vacuo. The residue is an oil which gradually solidifies and which is used without further purification for the following chlorination.

Example 2

4-Methoxy-3-chloromethyl-N-dimethylaminomethylenephenylsulfonamide

The product described above is mixed with 0.4 ml of thionyl chloride in 5 ml of toluene and stirred at 60° C. for 3 hours. After the volatiles have been stripped off in vacuo, the residue is extracted in ethyl acetate with 1N sodium hydroxide solution, and the organic phase is washed with water, dried over sodium sulfate and concentrated in vacuo.

Example 3

N-Dimethylaminomethylene-4-methoxy-3-[(3,3,5-trimethylcyclohexylamino)methyl]-benzenesulfonamide A mixture of 0.2 g of 4-methoxy-3-chloromethyl-N-dimethylaminomethylenephenylsulfon-amide, 0.37 ml of 3,3,5-trimethylcyclohexylamine and 5 ml of methylene chloride is stirred at RT for 24 hours and then concentrated in vacuo.

The residue is taken up in ethyl acetate and extracted with water, and the organic phase is dried over sodium sulfate and concentrated.

m.p.: oil

Unless indicated otherwise, the following examples were prepared in analogy to Examples 1 to 3.

Example 4

N-Dimethylaminomethylene-4-methoxy-3-[(3,5-dimethylphenoxy)methyl]benzenesulfonamide m.p.: oil

Example 5

N-Dimethylaminomethylene-4-methoxy-3-[(3,3,5-trimethylcyclohexylamino)methyl]-N-methylsulfonylbenzenesulfonamide m.p.: oil

Example 6

N-Dimethylaminomethylene-4-methoxy-3-dibutylaminomethylbenzenesulfonamide m.p.: oil

Example 7

N-Dimethylaminomethylene-4-methoxy-3-(4-benzylpiperazinomethyl)benzenesulfonamide m.p.: oil

Example 8

N-Dimethylaminomethylene-4-methoxy-3-[(3,5-dimethylpiperidino)methyl]benzenesulfonamide m.p.: 89° C.

Example 9

N-Dimethylaminomethylene-4-methoxy-3-[(2-benzylphenoxy)methyl]benzenesulfonamide This compound is obtained as an oil in analogy to Example 3 starting from 2-benzylphenol, sodium hydride and 4-methoxy-3-chloromethyl-N-dimethylaminomethylenephenylsulfonamide in tetrahydrofuran.

Example 10

4-Chloro-3-(dimethylaminomethylenesulfamoyl)-N-(3,3,5-trimethylcyclohexyl)benzamide m.p.: 180° C.

Example 11

4-Chloro-3-(dimethylaminomethylenesulfamoyl)-N-(2,2,6,6-tetramethylpiperidin-4-yl)-benzamide m.p.: 192° C.

Example 12

4-Chloro-3-(dimethylaminomethylenesulfamoyl)-N-(3,5-dimethylphenyl)benzamide m.p.: 216° C.

Example 13

4-Chloro-3-(dimethylaminomethylenesulfamoyl)benzoic acid (cis-2,6-dimethyl-morpholide)

m.p.: oil

Example 14

4-Chloro-3-(dimethylaminomethylenesulfamoyl)benzoic acid (3,3-dimethylpiperidide)

m.p.: oil

Example 15

4-Chloro-3-(dimethylaminomethylenesulfamoyl)-N-(2,2-dimethylpropyl)benzamide m.p.: resin

Example 16

4-Chloro-3-(dimethylaminomethylenesulfamoyl)-N-(2-chlorophenyl methyl)benzamide m.p.: 167° C.

Example 17

4-Chloro-3-(N-methylpiperazinomethylenesulfamoyl)-N-(3,3,5-dimethylcyclohexyl)benzamide This product is obtained as a yellow oil by heating 4-chloro-3-(dimethylaminomethylenesulfamoyl)-N-(3,3,5-trimethylcyclohexyl)benzamide with N-methylpiperazine in N-methylpyrrolidone at 100° C. and by working up by column chromatography (silica gel, methylene chloride:methanol=95:5).

Example 18

6-Chloro-N-dimethylaminomethylene-3-[(3,3-dimethylpiperidino)methyl]benzenesulfonamide m.p.: oil

Example 19

6-Chloro-N-dimethylaminomethylene-3-[(3,5-dimethylphenoxy)methyl]benzenesulfonamide m.p.: 137° C.

Example 20

6-Chloro-N-dimethylaminomethylene-3-[(3,3,5-trimethylcyclohexylamino)methyl]benzenesulfonamide m.p.: oil

Example 21

6-Chloro-N-dimethylaminomethylene-3-[(N-(3,3,5-trimethylcyclohexyl)-N-methylsulfonylamino)methyl]benzenesulfonamide This compound is obtained as an oil by reacting 6-chloro-N-dimethylaminomethylene-3-[(3,3,5-trimethylcyclohexylamino)methyl]benzenesulfonamide with methanesulfonyl chloride in methylene chloride in the presence of pyridine as auxiliary base and by purification by column chromatography (silica gel, methylene chloride:methanol=95:5).

Example 22

6-Chloro-3-(3,3,5-trimethylcyclohexylaminosulfonyl)benzenesulfonamide

Intermediate

A mixture consisting of 2.9 g of 6-chloro-3-chlorosulfonylbenzenesulfonamide, 1.4 ml of triethylamine, 1.7 ml of 3,3,5-trimethylcyclohexylamine and 30 ml of tetrahydrofuran is stirred at RT for 24 hours. After concentration in vacuo, the residue is stirred with isopropanol and the solid is filtered off with suction, washed with water and dried in vacuo at 40° C.

m.p.: 100° C.

Example 23

6-Chloro-N-dimethylaminomethylene-3-(3,3,5-trimethylcyclohexylaminosulfonyl]benzenesulfonamide is obtained by reacting 6-chloro-3-(3,3,5-trimethylcyclohexylaminosulfonyl]-benzenesulfonamide with dimethylformamide dimethyl acetal in DMF at 80° C.

m.p.: 100° C.

Example 24

6-Chloro-N-dimethylaminomethylene-3-(3,3-dimethylpiperidinosulfonyl]-benzenesulfonamide is obtained in analogy to Example 22 and 23.

m.p.: 123° C.

Example 25

4-Chloro-N-butylaminomethylene-3-[3,3,5-trimethylcyclohexylaminosulfonyl]benzenesulfonamide is obtained by reacting 6-chloro-N-dimethylaminomethylene-3-(3,3,5-trimethylcyclohexylaminosulfonyl]benzenesulfonamide with butylamine in N-methylpyrrolidone.

m.p.: oil

Example 26

2-Amino-4-trifluoromethyl-5-dimethylaminomethylenesulfamoyl-N-(3,3,5-trimethyl-cyclohexyl)benzenesulfonamide m.p.: >165° C. (decomp.)

Example 27

2-Amino-4-chloro-5-(dimethylaminomethylenesulfamoyl)benzenesulfonyl chloride (intermediate)

4 g of 6-chloro-N-dimethylaminomethylene 1,1-dioxo-1,2,3,4-tetrahydro-5,6-benzo[1,2,4]thiadiazine-7-sulfonamide are added to chlorosulfonic acid (15 mL) at 70° C., and the mixture stirred at 80° C. for 1.5 h, then added dropwise to ice-water and stirred for 15 min. The solid is filtered off and dried and used without further purification for further reactions.

Example 28

2-Amino-4-chloro-5-dimethylaminomethylenesulfamoyl-N-dibutylbenzenesulfonamide

A solution of 2-amino-4-chloro-5-(dimethylaminomethylenesulfamoyl)benzenesulfonyl chloride (120 mg, 0.33 mmol) in acetone (1 mL) is mixed with dibutylamine and stirred at RT for 1.5 h. The mixture is concentrated in vacuo, triturated with n-heptane and filtered off with suction.

m.p.: 145° C. (decomp.)

Example 29

2-Amino-4-chloro-5-dimethylaminomethylenesulfamoyl-N-diisobutylbenzenesulfonamide m.p.: 126° C.

Example 30

2-Amino-4-chloro-5-dimethylaminomethylenesulfamoylbenzenesulfonylpiperidine m.p.: 103° C.

Example 31

2-Amino-4-chloro-5-dimethylaminomethylenesulfamoylbenzenesulfonylpiperazine m.p.: 96° C.

Example 32

2-Amino-4-chloro-5-dimethylaminomethylenesulfamoyl-N-(3,3,5-trimethylcyclohexylbenzenesulfonamide m.p.: 100° C.

Example 33

2-Amino-4-chloro-5-dimethylaminomethylenesulfamoyl-N-cyclohexyl-N-allyl-benzenesulfonamide m.p.: 90° C.

Example 34

2-Amino-4-chloro-5-dimethylaminomethylenesulfamoyl-N-cyclohexyl-N-isopropyl-benzenesulfonamide m.p.: 122° C. (decomp.)

Example 35

2-Amino-4-chloro-5-dimethylaminomethylenesulfamoyl-N-cyclohexyl-N-ethylbenzenesulfonamide m.p.: oil

Example 36

2-Amino-4-chloro-5-dimethylaminomethylenesulfamoyl-N-(2-methyl heptyl)-benzenesulfonamide m.p.: oil

Example 37

2-Amino-4-chloro-5-dimethylaminomethylenesulfamoyl-N-hexyl-benzenesulfonamide m.p.: oil

Example 38

2-Amino-4-chloro-5-dimethylaminomethylenesulfamoyl-N-octylbenzenesulfonamide m.p.: 110° C.

Example 39

2-Amino-4-chloro-5-dimethylaminomethylenesulfamoyl-N-nonylbenzenesulfonamide m.p.: oil

Example 40

2-Amino-4-chloro-5-dimethylaminomethylenesulfamoyl-N-decylbenzenesulfonamide m.p.: oil

Example 41

2-Amino-4-trifluoromethyl-5-dimethylaminomethylenesulfamoyl-N-decylbenzenesulfonamide m.p.: oil

Example 42

2-Amino-4-trifluoromethyl-5-dimethylaminomethylenesulfamoyl-N-nonylbenzenesulfonamide m.p.: oil

Example 43

2-Amino-4-trifluoromethyl-5-dimethylaminomethylenesulfamoyl-N-octylbenzenesulfonamide m.p.: oil

Example 44

2-Amino-4-trifluoromethyl-5-dimethylaminomethylenesulfamoyl-N-hexylbenzenesulfonamide m.p.: oil

Example 45

2-Amino-5-dimethylaminomethylenesulfamoyl-N-cyclohexyl benzenesulfonamide m.p.: 156° C.

Example 46

2-Amino-4-chloro-5-dimethylaminomethylenesulfamoyl-N-cyclopentylbenzenesulfonamide m.p.: oil

Example 47

2-Amino-4-chloro-5-dimethylaminomethylenesulfamoyl-N-(ethoxycarbonylmethyl)benzenesulfonamide m.p.: oil

Example 48

2-Amino-4-trifluoromethyl-5-dimethylaminomethylenesulfamoyl-N-cyclohexyl-benzenesulfonamide m.p.: >185° C. (decomp.)

Biochemical Investigations

The effect of the compounds of the invention of the formula I is tested in the following enzyme assay system:

Enzyme Preparation:

Preparation of the Partially Purified HSL:

Isolated rat fat cells are obtained from epididymal adipose tissue from untreated male rats (Wistar, 220-250 g) by collagenase treatment in accordance with published methods (e.g. S, Nilsson et al., Anal. Biochem. 158, 1986, 399-407; G.

Fredrikson et al., J. Biol. Chem. 256, 1981, 6311-6320; H. Tornquist et al., J. Biol. Chem. 251, 1976, 813-819). The fat cells from 10 rats are washed three times by flotation with 50 ml of homogenization buffer (25 ml Tris/HCl, pH 7.4, 0.25 M sucrose, 1 mM EDTA, 1 mM DTT, 10 µg/ml leupeptin, 10 µg/ml antipain, 20 µg/ml pepstatin) each time and finally taken up in 10 ml of homogenization buffer. The fat cells are homogenized in a Teflon-in-glass homogenizer (Braun-Melsungen) by 10 strokes at 1500 rpm and 15° C. The homogenate is centrifuged (Sorvall SM24 tubes, 5000 rpm, 10 min, 4° C.). The subnatant between the layer of fat at the top and the pellet is removed and the centrifugation is repeated. The subnatant resulting therefrom is centrifuged again (Sorvall SM24 tubes, 20 000 rpm, 45 min, 4° C.). The subnatant is removed, and 1 g of heparin-Sepharose (Pharmacia-Biotech, CL-6B, washed 5× with 25 mM Tris/HCl, pH 7.4, 150 mM NaCl) is added. After incubation at 4° C. for 60 min (shaking at intervals of 15 min), the mixture is centrifuged (Sorvall SM24 tubes, 3000 rpm, 10 min, 4° C.). The supernatant is adjusted to pH 5.2 by adding glacial acetic acid and is incubated at 4° C. for 30 min. The precipitates are collected by centrifugation (Sorvall SS34, 12 000 rpm, 10 min, 4° C.) and suspended in 2.5 ml of 20 mM Tris/HCl, pH 7.0, 1 mM EDTA, 65 mM NaCl, 13% sucrose, 1 mM DTT, 10 µg/ml leupeptin/pepstatin/antipain. The suspension is dialyzed against 25 mM Tris/HCl, pH 7.4, 50% glycerol, 1 mM DTT, 10 µg/ml leupeptin, pepstatin, antipain at 4° C. overnight and then loaded onto a hydroxiapatite column (0.1 g per 1 ml of suspension, equilibrated with 10 mM potassium phosphate, pH 7.0, 30% glycerol, 1 mM DTT). The column is washed with four volumes of equilibration buffer at a flow rate of 20 to 30 ml/h. The HSL is eluted with one volume of equilibration buffer containing 0.5 M potassium phosphate and then dialyzed (see above) and concentrated 5- to 10-fold by ultrafiltration (Amicon Diaflo PM 10 Filter) at 4° C. The partially purified HSL can be stored at −70° C. for 4 to 6 weeks.

Substrate Preparation:

Preparation of NAG (NBD Monoacyl Glyceride) Substrate:

6 mg of phosphatidylcholine and 6 mg of phosphatidylinositol are each dissolved in 1 ml of chloroform. 10 mg of NAG are dissolved in 1 ml of chloroform. Two parts of phosphatidylinositol solution (e.g. 83.5 µl) and one part of phosphatidylcholine solution (e.g. 41.5 µl) and 100 µl of NAG solution are pipetted together into plastic scintillation vessels (final concentration in the assay: 0.0375 mg of phospholipid/ml; 0.05 mg/NAG/ml). The chloroform (225 µl total volume) is completely removed by passing a stream of $N_2$ over it. The dried substrate can be stored at 4° C. for up to 3 days. To prepare the phospholipid vesicles/micelles with intercalated NAG (on the day of the assay), the dried substrate is taken up in 20 ml of assay buffer (25 mM Tris/HCl, pH 7.4; 150 mM NaCl) and two ultrasound treatments carried out with an ultrasonic probe (Branson Sonifier Type II, standard microtip): 1st treatment setting 2, 2×1 min, in between 1 min on ice each time; 2nd treatment setting 4, 2×1 min, in between 1 min on ice each time. During this procedure, the color of the substrate solution changes from yellow (extinction maximum 481 nm) to red (extinction maximum 550 nm) owing to intercalation of NAG between the phospholipid molecules in the vesicles/micelles. Before use as substrate (within the next 2 h), the solution is incubated on ice for 15 min.

Indirect NAG Assay:

The assay is carried out in 1.5 ml Eppendorf vessels or 96-well plates at 30° C. for 60 min. To find HSL inhibitors, 10 µl of the test substance are introduced into assay buffer (25 mM Tris/HCl, pH 7.4; 150 mM NaCl) in the presence of 16.6% DMSO. 180 µl of the substrate solution (20 µg/ml phosphatidylcholine, 10 µg/ml phosphatidylinositol, 50 µg/ml NAG in assay buffer) are added. After preincubation at 30° C. for 15 min, 20 µl of the enzyme solution in assay buffer (diluted 1- to 4-fold) are pipetted in, and the extinction at 480 nm is immediately measured in a cuvette photometer (0.5 ml cuvette) or microtiter plate reader. After incubation at 30° C. for 60 min, the extinction is measured again. The increase in extinction at 480 nm is a measure of the enzymic activity. Under standard conditions, 20 µg of partially purified HSL lead to a change of 0.4=4000 arb. units in extinction.

Direct NAG Assay:

As an alternative to measurement of the change in extinction of the substrate solution, the products of the HSL reaction are investigated by phase separation/thin-layer chromatography. For this purpose, 1.3 ml of methanol/chloroform/heptane (10:9:7) and then 0.4 ml of 0.1 M NaOH are added to the incubation mixture (200 µl total volume, see indirect NAG assay) in 2 ml Eppendorf vessels. After vigorous mixing (10 sec), phase separation is initiated by centrifugation (800×g, 20 min, room temperature). Equivalent volumes (e.g. 0.4 ml) are taken from the aqueous upper phase, and the extinction at 481 nm is determined in a photometer. For thin-layer chromatography, the aqueous phase is dried (SpeedVac) and then taken up in 50 µl of tetrahydrofuran. 5 µl samples are loaded onto silica gel Si-60 plates (Merck). The chromatography is carried out with 78 ml of diethyl ether/22 ml of petroleum ether/1 ml of glacial acetic acid as mobile phase. The amount of liberated fluorescent NBD-fatty acid is determined by Phosphorimaging (Molecular Dynamics, Storm 840 and ImageQuant Software) at an excitation wavelength of 460 nm and emission wavelength of 540-560 nm.

Evaluation:

Substances are normally tested in four independent mixtures. The inhibition of the HSL enzymatic activity by a test substance is determined by comparing with an uninhibited control reaction. The $IC_{50}$ is calculated from an inhibition plot with min. 10 concentrations of the test substance. The GRAPHIT, Elsevier-BIOSOFT software package is used to analyze the data.

The compounds showed the following effect in this assay:

| Compound of Example No. | $IC_{50}$ (µM) |
|---|---|
| 19 | 0.40 |
| 21 | 0.50 |
| 23 | 0.15 |
| 28 | 0.03 |
| 29 | 0.70 |
| 32 | 0.001 |
| 33 | 0.20 |
| 48 | 0.70 |

The invention claimed is:

1. A compound of formula (I)

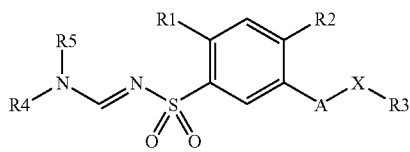

wherein:
R1 is hydrogen, halogen or —CF$_3$;
R2 is hydrogen, —NH$_2$, —NH(C$_1$-C$_3$-alkyl), —N(C$_1$-C$_3$-alkyl)$_2$ or C$_1$-C$_3$-alkoxy and R1 and R2 may not simultaneously be hydrogen, wherein the alkyl and alkoxy moieties are unsubstituted;
R3 is unsubstituted or monosubstituted C$_1$-C$_{10}$-alkyl, C$_2$-C$_{10}$-alkenyl, aryl, heterocyclyl or heteroaryl,
where the substituents are selected from the group consisting of:
aryl, heteroaryl, heterocyclyl, aryl-(C$_1$-C$_6$-alkyl)-, heterocyclyl-(C$_1$-C$_6$-alkyl) -, heteroaryl-(C$_1$-C$_6$-alkyl)-, —O -aryl, fluorine, chlorine, bromine, —CF$_3$, —OCF$_3$, —NO$_2$, —CN, —C(O)R7, hydroxy, C$_1$-C$_6$-alkyl and C$_1$-C$_3$-alkoxy,
and the aryl, heteroaryl and heterocyclyl fragments of these substituents may in turn be substituted by a substituent selected from the group consisting of fluorine, chlorine, bromine, oxo, —CF$_3$, —OCF$_3$, —NO$_2$, —CN, hydroxy, C$_1$-C$_3$-alkyl and C$_1$-C$_3$-alkoxy;
R4 and R5 are, independently of one another, hydrogen, unsubstituted or substituted C$_1$-C$_{10}$-alkyl or aryl-(C$_1$-C$_6$-alkyl)-,
where the substituents are selected from the group consisting of:
aryl, heteroaryl, heterocyclyl, aryl-(C$_1$-C$_6$-alkyl)-, heterocyclyl-(C$_1$-C$_6$-alkyl)-, heteroaryl-(C$_1$-C$_6$-alkyl)-, —O-aryl, fluorine, chlorine, bromine, —CF$_3$, —OCF$_3$, —NO$_2$, —CN, —C(O)R7, hydroxy, C$_1$-C$_6$-alkyl and C$_1$-C$_3$-alkoxy,
and the aryl, heteroaryl and heterocyclyl fragments of these substituents may in turn be substituted by a substituent selected from the group consisting of fluorine, chlorine, bromine, oxo, —CF$_3$, —OCF$_3$, —NO$_2$, —CN, hydroxy, C$_1$-C$_3$-alkyl or C$_1$-C$_3$-alkoxy; or
R4 and R5 form, together with the nitrogen atom to which they are bonded, an unsubstituted or substituted heterocyclyl,
where the substituents are selected from:
halogen, C$_1$-C$_6$-alkyl, C$_1$-C$_6$-alkoxy, phenyl, oxo, —NH$_2$, —NH(C$_1$-C$_3$-alkyl), —N(C$_1$-C$_3$-alkyl)$_2$, —OCF$_3$, —CF$_3$ and hydroxy;
R6 is hydrogen, —SO$_2$(C$_1$-C$_3$-alkyl), unsubstituted or substituted C$_1$-C$_{10}$-alkyl, C$_2$-C$_{10}$-alkenyl or aryl-(C$_1$-C$_6$-alkyl)-,
where the substituents are selected from:
halogen, C$_1$-C$_6$-alkyl, C$_1$-C$_6$-alkoxy, phenyl, oxo, —NH$_2$, —NH(C$_1$-C$_3$-alkyl), —N(C$_1$-C$_3$-alkyl)$_2$, —OCF$_3$, —CF$_3$ and hydroxy; or
R6 forms, together with R3 and X, if X is N, unsubstituted or substituted heterocyclyl,
where the substituents are selected from the group consisting of:
aryl, heteroaryl, heterocyclyl, aryl-(C$_1$-C$_6$-alkyl)-, heterocyclyl-(C$_1$-C$_6$-alkyl) -, heteroaryl-(C$_1$-C$_6$-alkyl)-, -O-aryl, fluorine, chlorine, bromine, -CF$_3$, —OCF$_3$, —NO$_2$, —CN, —C(O)R7, hydroxy, C$_1$-C$_6$-alkyl and C$_1$-C$_3$-alkoxy,
and the aryl, heteroaryl and heterocyclyl fragments of these substituents may in turn be substituted by a substituent selected from the group consisting of fluorine, chlorine, bromine, oxo, —CF$_3$, —OCF$_3$, —NO$_2$, —CN, hydroxy, C$_1$-C$_3$-alkyl and C$_1$-C$_3$-alkoxy;
R7 is C$_1$-C$_3$-alkoxy, —O-phenyl, C$_1$-C$_3$-alkyl, —NH$_2$, —NH(C$_1$-C$_3$-alkyl), —N(C$_1$-C$_3$-alky1)$_2$ or phenyl,
and the phenyl fragments of R7 may in turn be substituted by a substituent selected from the group consisting of fluorine, chlorine, bromine, —CF$_3$, —OCF$_3$, —NO$_2$, —CN, hydroxy, C$_1$-C$_3$-alkyl and C$_1$-C$_3$-alkoxy;
A is CO or CH$_2$;
X is NR6 or O; and
wherein
heteroaryl is a 5 to 10-membered, aromatic, mono-r bicyclic heterocycle which comprises one or more heteroatoms selected from N, O and S;
aryl is a 5 to 10-membered aromatic mono- or bicyclic system; and
heterocyclyl is a 5 to 10-membered, nonaromatic, mono- or bicyclic heterocycle which comprises one or more heteroatoms selected from N, O and S;
or a physiologically tolerated salt thereof;
with the proviso that when R2 is hydrogen and R1 is halogen, then —A—X—R3 is not i) —C(O)—O—CH$_2$—CH$_2$—NH$_2$, ii) —C(O) —NH—CH$_2$—CH=CH$_2$, iii) —C(O) —NH—CH$_2$—CH$_2$—Z with Z equal to halogen, hydroxy, trialkylammonium, mesylate or tosylate, iv) —C(O) —O—(C$_1$-C$_6$-alkyl), v) —C(O) —NH-benzimidazolyl or vi) —C(O) —NH-(1,2,3,4-tetrahydroisoquinolinyl), where the —CH$_2$—CH$_2$-fragment in i) and iii) may be substituted by 1 to 4 alkyl radicals R$^1$ to R$^4$ each having 1 to 4 carbon atoms, where one of the radicals R$^1$ to R$^4$ may also be a carboxy, hydroxymethyl or an alkyloxycarbonyl group having not more than 5 carbon atoms or one or two of the radicals R$^1$ to R$^4$ may be isopropyl, isobutyl, tert-butyl, phenyl or cycloalkyl having 5 to 6 carbon atoms, and where the benzimidazolyl and the (1,2,3,4-tetrahydroisoquinolinyl) fragment in v) and vi) may be unsubstituted or at least monosubstituted.

2. The compound as claimed in claim 1, wherein:
R1 is hydrogen, halogen or —CF$_3$;
R2 is hydrogen, —NH$_2$, —NH(C$_1$-C$_3$-alkyl), —N(C$_1$-C$_3$-alkyl)$_2$ or C$_1$-C$_3$-alkoxy and R1 and R2 may not simultaneously be hydrogen, wherein the alkyl and alkoxy moieties are unsubstituted;
R3 is unsubstituted or substituted C$_1$-C$_{io}$-alkyl, C$_2$-C$_6$-alkenyl, aryl or heterocyclyl,
where the substituents are selected from the group consisting of:
aryl, aryl-(C$_1$ -C$_6$-alkyl)-, fluorine, chlorine, bromine, —CF$_3$, —C(O)O—(C$_1$ -C$_3$-alkyl), —C(O)O-phenyl, hydroxy, C$_1$ -C$_3$ -alkyl and C$_1$ -C$_3$ -alkoxy;
R4 and R5 are, independently of one another, hydrogen, unsubstituted or substituted C$_1$ -C$_{10}$-alkyl, where the substituents are selected from:
halogen, $C_1$-$C_6$-alkoxy, —$CF_3$ and hydroxyl; or
R4 and R5 form, together with the nitrogen atom to which they are bonded,
unsubstituted or substituted heterocyclyl,
where the substituents are selected from:
halogen, $C_1$-$C_6$-alkyl, $C_1$-$C_6$-alkoxy, —$CF_3$ and hydroxy;
R6 is hydrogen, —$SO_2$($C_1$-$C_3$-alkyl), unsubstituted or substituted $C_1$-$C_{10}$-alkyl or $C_2$-$C_6$-alkenyl,
where the substituents are selected from:
halogen, $C_1$-$C_6$-alkoxy and —$CF_3$; or
R6 forms, together with R3 and X, if X is equal to N, unsubstituted or substituted heterocyclyl,
where the substituents are selected from the group consisting of:
aryl, aryl-($C_1$-$C_6$-alkyl)-, fluorine, chlorine, bromine, —$CF_3$, —C(O)O—($C_1$-$C_3$-alkyl), —C(O)O-phenyl, hydroxy, $C_1$-$C_3$-alkyl and $C_1$-$C_3$-alkoxy,
and the aryl fragments of these substituents may in turn be substituted by fluorine, chlorine, bromine, oxo, —$CF_3$, hydroxy, $C_1$-$C_3$-alkyl or $C_1$-$C_3$-alkoxy;
A is CO or $CH_2$;
X is NR6 or O;
aryl is phenyl, indanyl or naphthyl; and
heterocyclyl is morpholinyl, pyrrolidinyl, piperidinyl, tetrahydropyranyl, thiazolidinyl, dihydroisoxazolyl, piperazinyl or tetrahydrofuranyl;
or a physiologically acceptable salt thereof.

3. The compound as claimed in claim 1, where:
R1 is chlorine or —$CF_3$;
R2 is hydrogen or —$NH_2$;
R3 is unsubstituted or substituted $C_1$-$C_6$-alkyl, $C_2$-$C_3$-alkenyl or phenyl,
where the substituents are selected from: $C_1$-$C_3$-alkyl, $C_1$-$C_3$-alkoxy, chlorine, fluorine and hydroxy;
R4 and R5 are each methyl;
R6 is hydrogen, —$SO_2CH_3$ or $C_1$-$C_6$-alkyl;
A is $CH_2$; and
X is NR6 or O;
or a physiologically acceptable salt thereof.

4. A pharmaceutical composition comprising the compound as claimed in claim 1, or a physiologically acceptable salt thereof and a physiologically acceptable carrier.

5. A method of inhibiting monoacylglyeride lipase or hormone-sensitive lipase comprising administering to a patient in need thereof an effective amount of the compound as claimed in claim 1, or a physiologically acceptable salt thereof.

6. A method for treating non-insulin-dependent diabetes mellitus, diabetic syndrome or obesity which comprises administering to a patient in need thereof an effective amount of the compound as claimed in claim 1, or a physiologically acceptable salt thereof.

7. The pharmaceutical composition as claimed in claim 4, in the form of a pill, tablet, coated tablet, suckable tablet, granules, capsule, hard or soft gelatin capsule, aqueous solutions, alcoholic solution, oily solution, syrup, emulsion, suspension, pastille, solution for injection or infusion, ointment, tincture, cream, lotion, dusting powder, spray, transdermal therapeutic system, nasal spray, aerosol, aerosol mixture, microcapsule, implant, rod or patch.

8. A process for preparing the compound of formula (I) as claimed in claim 1, which comprises:

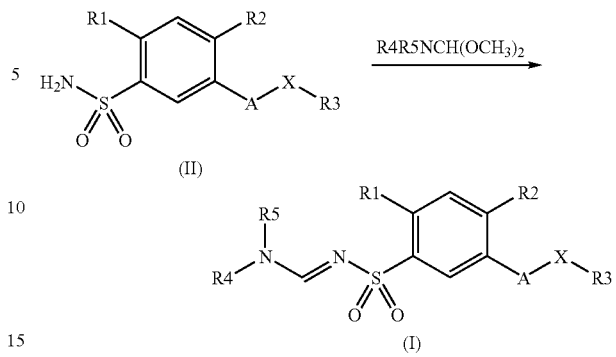

reacting a compound of formula (II) in a solvent with $R4R5NCH(OCH_3)_2$.

9. A process for preparing the compound of formula (I) as claimed in claim 1, which comprises:

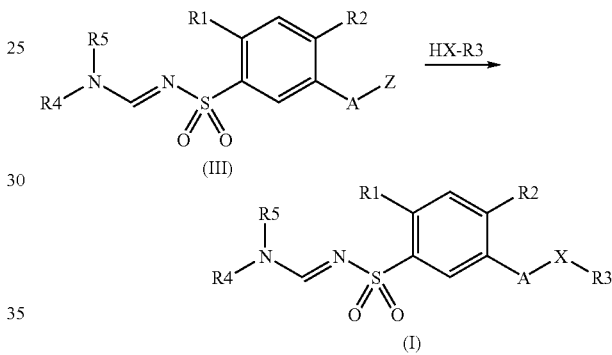

reacting a compound of formula (III), wherein A—Z is selected from COCl, $CH_2Cl$ and $CH_2Br$, with HX-R3 in an inert solvent.

10. A pharmaceutical composition comprising the compound as claimed in claim 2, or a physiologically acceptable salt thereof and a physiologically acceptable carrier.

11. A pharmaceutical composition comprising the compound as claimed in claim 3, or a physiologically acceptable salt thereof and a physiologically acceptable carrier.

12. The compound according to claim 1, which is:
4-Chloro-3-(dimethylaminomethylenesulfamoyl)—N-(3,3,5-trimethylcyclohexyl)benzamide;
4-Chloro-3-(dimethylaminomethylenesulfamoyl)—N-(2,2,6,6-tetramethylpiperidin-4-yl)benzamide;
4-Chloro-3-(dimethylaminomethylenesulfamoyl)-N-(3,5-dimethylphenyl)benzamide;
4-Chloro-3-(dimethylaminomethylenesulfamoyl)benzoic acid (cis-2,6-dimethyl-morpholide);
4-Chloro-3-(dimethylaminomethylenesulfamoyl)benzoic acid (3,3-dimethyl-piperidide);
4-Chloro-3-(dimethylaminomethylenesulfamoyl)—N-(2,2-dimethylpropyl)benzamide;
4-Chloro-3-(dimethylaminomethylenesulfamoyl)—N-(2-chlorophenylmethyl)benzamide; or 4-Chloro-3-(N-methylpiperazinomethylenesulfamoyl)—N-(3,3,5-dimethylcyclohexyl)benzamide;
or a physiologically acceptable salt thereof.

13. A pharmaceutical composition comprising the compound as claimed in claim 12, or a physiologically acceptable salt thereof and a physiologically acceptable carrier.

14. A method of inhibiting monoacylglyeride lipase or hormone-sensitive lipase comprising administering to a patient in need thereof an effective amount of the compound as claimed in claim 2, or a physiologically acceptable salt thereof.

15. A method of inhibiting monoacylglyeride lipase or hormone- sensitive lipase comprising administering to a patient in need thereof an effective amount of the compound as claimed in claim 3, or a physiologically acceptable salt thereof.

16. A method of inhibiting monoacylglyeride lipase or hormone- sensitive lipase comprising administering to a patient in need thereof an effective amount of the compound as claimed in claim 12, or a physiologically acceptable salt thereof.

* * * * *